US009659405B2

(12) United States Patent
Wahrenberg

(10) Patent No.: US 9,659,405 B2
(45) Date of Patent: May 23, 2017

(54) IMAGE PROCESSING METHOD AND APPARATUS

(71) Applicant: Toshiba Medical Systems Corporation, Otawara-shi (JP)

(72) Inventor: Magnus Fredrik Wahrenberg, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/676,056

(22) Filed: Apr. 1, 2015

(65) Prior Publication Data

US 2016/0292913 A1    Oct. 6, 2016

(51) Int. Cl.
*G06K 9/00*    (2006.01)
*G06T 15/50*   (2011.01)
(Continued)

(52) U.S. Cl.
CPC ............ *G06T 15/506* (2013.01); *A61B 6/466* (2013.01); *A61B 8/483* (2013.01); *A61B 8/5215* (2013.01); *G06T 5/009* (2013.01); *G06T 15/08* (2013.01); *A61B 5/055* (2013.01); *A61B 6/032* (2013.01); *G06T 2207/10081* (2013.01); *G06T 2207/10088* (2013.01); *G06T 2207/10104* (2013.01); *G06T 2207/10108* (2013.01); *G06T 2207/20208* (2013.01); *G06T 2207/30004* (2013.01)

(58) Field of Classification Search
USPC ........ 382/100, 103, 106–107, 128–133, 154, 382/162, 168–173, 181, 199, 219, 224, 382/232, 254, 274, 276, 285–295, 305, 382/312; 345/424; 600/443, 118
See application file for complete search history.

(56) References Cited

U.S. PATENT DOCUMENTS

2009/0012361 A1* 1/2009 MacKinnon ....... A61B 1/00186
                                                  600/118
2009/0251464 A1* 10/2009 Matsumoto ............. G06T 15/06
                                                  345/424
(Continued)

FOREIGN PATENT DOCUMENTS

JP    2007-241746    9/2007
JP    2008-259697    10/2008
JP    2014-61288     4/2014

OTHER PUBLICATIONS

Fly Thru, Aplio 500 brochure, 2012, p. 12, http://www.toshibamedicalsystems.com/tmd/english/products/uslpdf/brochure_aplio500.pdf.

*Primary Examiner* — Seyed Azarian
(74) *Attorney, Agent, or Firm* — Oblon, McClelland, Maier & Neustadt, L.L.P.

(57) ABSTRACT

An image processing apparatus comprises data receiving circuitry for receiving a volumetric imaging data set which is representative of a volume, the volume comprising a region of interest and lighting circuitry configured to place a virtual light source outside the region of interest and to apply a lighting simulation process to simulate light from the virtual light source. The applying of the lighting simulation process is at least partially different for a first lighting region than for a second lighting region, the first lighting region comprising at least part of the volume outside the region of interest and the second lighting region comprising at least part of the region of interest.

42 Claims, 8 Drawing Sheets

(51) Int. Cl.
*A61B 8/08* (2006.01)
*G06T 5/00* (2006.01)
*G06T 15/08* (2011.01)
*A61B 6/00* (2006.01)
*A61B 8/00* (2006.01)
*A61B 6/03* (2006.01)
*A61B 5/055* (2006.01)

(56) References Cited

U.S. PATENT DOCUMENTS

2011/0116692 A1\* 5/2011 Dekel .................... G06T 15/08
　　　　　　　　　　　　　　　　　　　382/128
2014/0232719 A1\* 8/2014 Wahrenberg .......... G06T 15/506
　　　　　　　　　　　　　　　　　　　345/424
2015/0164475 A1\* 6/2015 Kuga .................... A61B 8/463
　　　　　　　　　　　　　　　　　　　600/443

\* cited by examiner

IMAGE PROCESSING METHOD AND APPARATUS

FIELD

Embodiments described herein relate generally to a method of, and apparatus for simulating illumination in medical images, for example in an ultrasound image of a body cavity.

BACKGROUND

It is known to use ultrasound to image anatomical structures by transmission and reception of ultrasound waves from a transducer. Anatomical structures that are imaged by ultrasound may include interior structures of the body such as cavities, ducts, lumens and vessels. Interior structures of the body may comprise fluid-filled structures. In some circumstances, interior structures of the body may comprise structures that are normally air-filled but have been filled with a fluid (for example, with saline) for imaging purposes.

Three-dimensional (3D) ultrasound images may be obtained by using software to combine ultrasound data that has been taken at different positions or angles to obtain volumetric ultrasound data.

Other medical imaging modalities (for example, CT, MR, PET or SPECT imaging) may also be used to obtain three-dimensional data that is representative of interior structures of the body. The interior structures may comprise, for example, cavities, ducts, lumens, vessels or fluid-filled structures. Additionally, in some modalities the interior structures may comprise air-filled structures. The interior structures may comprise airways or lung cavities.

In addition, imaging modalities may use some type of contrast medium to enhance particular features. For example, micro bubble contrast may be used in ultrasound, iodine-based contrast may be used in CT, and gadolinium contrast may be used in MR.

Endoscopic views or flythrough views may be used in medical imaging applications to image cavities, ducts, vessels or other interior structures. An endoscopic view may be a view that simulates the view obtained in an endoscopy. An endoscopic view may refer to an examination for which previously, or alternatively, a real endoscope is used. In a real endoscopy, a camera is introduced into an interior structure of the body and the view from the camera is displayed on a screen. In contrast, in an endoscopic view of volumetric ultrasound data, a virtual camera is placed within an anatomical structure (for example, within a cavity) and the ultrasound data is rendered to produce an image of the anatomical structure that is viewed from the virtual camera position.

An endoscopic view may comprise a flythrough view. Additionally, the term flythrough view may be used to include images that display interior structures that are not commonly accessible using physical endoscopic devices.

A flythrough view may comprise an animated sequence of images such that the viewpoint appears to move through the interior structure. A flythrough view may make use of perspective projection such that proximal parts of the anatomical structure appear larger than distal parts. A flythrough view may make use of a fish-eye projection or one of a range of related angular projections.

A user may control navigation through the interior structure, for example by moving a virtual camera position through the interior structure. Flythrough may be used to explore lesions and ingrowing masses. Flythrough may be used to plan and follow up interventions such as placing stents or grafts.

Rendering an image from volumetric data may comprise placing one or more virtual light sources with respect to the coordinate system of the volumetric data and simulating light from the virtual light source or sources.

In some rendering methods, a virtual directional light source is used. A virtual directional light source may be a light that originates outside the volume represented by a volumetric data set that is being rendered, and that lights the volume with parallel rays coming from one direction. When lighting interior structures such as cavities, ducts or vessels, a virtual directional light source outside the volume may not be useful in some circumstances, because all or most of the light from the virtual directional light source may be absorbed before reaching the interior structure. Very little light may penetrate into the area of interest.

In some rendering methods, a virtual point light source is placed inside an anatomical structure of interest, for example inside a cavity. In a flythrough view, the position of the virtual point light source may in some circumstances be difficult to control. Even if the virtual point light source is attached to a virtual camera (simulating the position of the light source in endoscopy), it can be difficult to keep the point light source in a useful and sensible place. Occlusion may force the user to move the virtual point light source in three dimensions in order to obtain good lighting of the cavity. In some systems, input devices may have been constructed for two-dimensional operations and it may be difficult to use such input devices for placing a virtual light source in three dimensions. For example, an input device may be constructed so that a virtual light source position can be moved up and down and from side to side, but not in a perpendicular direction (which may be described as in and out of the screen).

Furthermore, the natural intensity fall-off from a point light (which falls off in intensity according to the inverse square law) may result in an excessive dynamic range in rendered images. Rendered images may be very bright in regions close to the point light source and very dark in regions that are further from the point light source. Structures near the point light source may cause shadowing of structures that are further away. A boundary of the anatomical structure of interest (for example, a lumen wall) may constrain the positioning of the point light source.

FIG. 1 illustrates a possible problem of using a point light with respect to intensity fall-off. A virtual point light source 2 illuminates a cavity 4. An image of the cavity is to be rendered from the position of virtual camera 6. Areas of the cavity that are near to the point source are very brightly illuminated, while areas of the cavity that are far from the point source are much less brightly illuminated. There may therefore be an excessively wide dynamic range in the rendered image.

BRIEF DESCRIPTION OF DRAWINGS

Embodiments are now described, by way of non-limiting example, and are illustrated in the following figures, in which.

DETAILED DESCRIPTION

Certain embodiments provide an image processing apparatus comprising data receiving circuitry for receiving a volumetric imaging data set which is representative of a volume, the volume comprising a region of interest. The image processing apparatus further comprises lighting circuitry configured to place a virtual light source outside the region of interest, and to apply a lighting simulation process to simulate light from the virtual light source. The applying of the lighting simulation process is at least partially different for a first lighting region than for a second lighting region, the first lighting region comprising at least part of the volume outside the region of interest and the second lighting region comprising at least part of the region of interest.

Certain embodiments provide an image processing method comprising receiving a volumetric imaging data set which is representative of a volume, the volume comprising a region of interest, placing a virtual light source outside the region of interest, and applying a lighting simulation process to simulate light from the virtual light source. The applying of the lighting simulation process is at least partially different for a first lighting region than for a second lighting region, the first lighting region comprising at least part of the volume outside the region of interest and the second lighting region comprising at least part of the region of interest.

Certain embodiments provide an image processing apparatus comprising data receiving circuitry for receiving a volumetric imaging data set which is representative of a volume and lighting circuitry configured to place at least one virtual light source relative to the volume and to apply a lighting simulation process to simulate light from the virtual light source. The lighting simulation process comprises simulating a plurality of rays emitted from the virtual light source, calculating irradiance resulting from the rays at each of an array of reference points in the volume, and adjusting the calculated irradiance for at least some of the array of reference points, thereby to modify a fall-off in irradiance with distance from the virtual light source.

Certain embodiments provide an image processing method comprising receiving a volumetric imaging data set which is representative of a volume, placing at least one virtual light source relative to the volume and applying a lighting simulation process to simulate light from the virtual light source. The lighting simulation process comprises simulating a plurality of rays emitted from the virtual light source, calculating irradiance resulting from the rays at each of an array of reference points in the volume, and adjusting the calculated irradiance for at least some of the array of reference points, thereby to modify a fall-off in irradiance with distance from the virtual light source.

Figure 2:
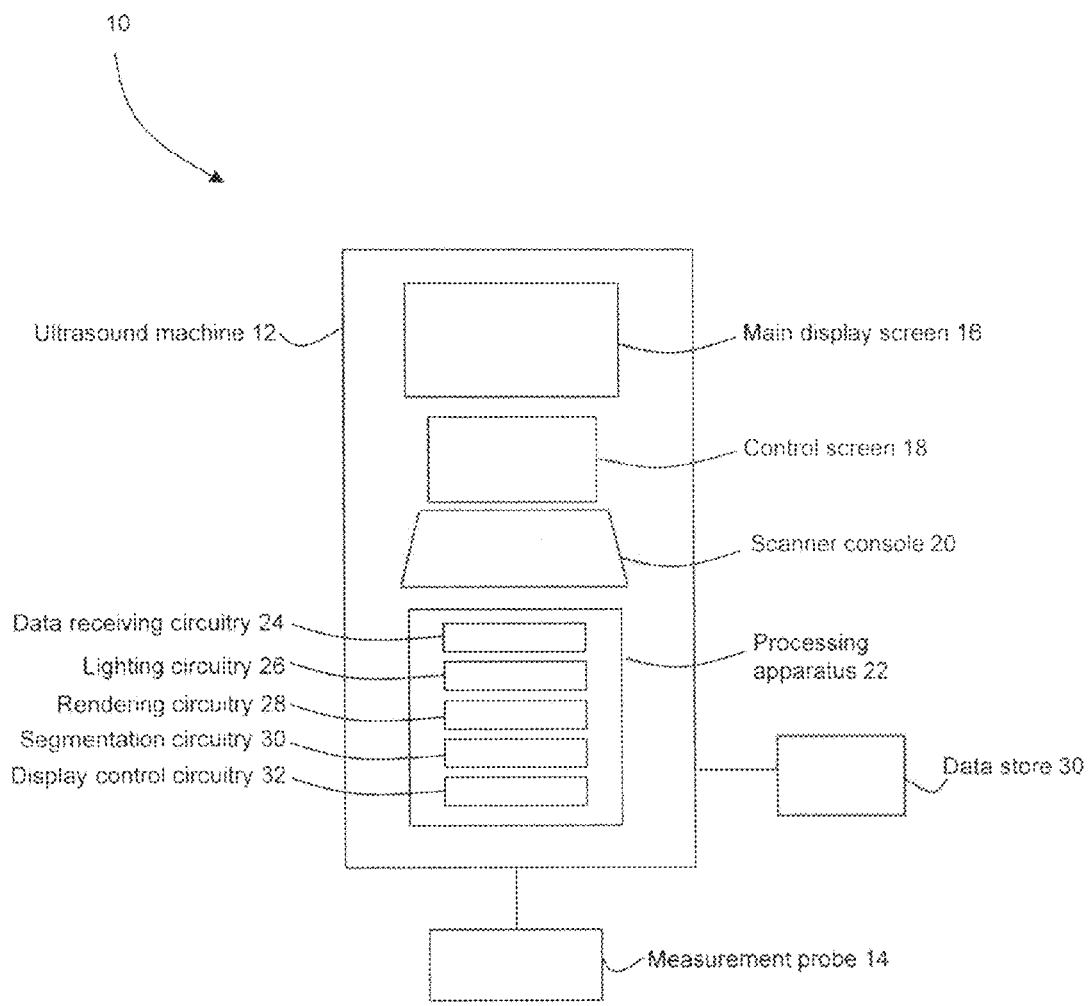
FIG. 2 is a schematic diagram of an apparatus according to an embodiment.

A medical diagnostic apparatus 10 according to an embodiment is illustrated schematically in FIG. 2. In the present embodiment, medical diagnostic apparatus 10 is configured to acquire volumetric data from a medical imaging scan, to process the acquired volumetric data and to render an image from the processed volumetric data. The medical diagnostic apparatus 10 may be described as an image processing apparatus, since a part of its function comprises image processing. In alternative embodiments, an apparatus (for example, an image processing apparatus) is configured to receive volumetric data that has been acquired by a scanner (such as an ultrasound machine, CT scanner, MR scanner, PET scanner or SPECT scanner), to process the received volumetric data and to render an image from the processed volumetric data.

In the present embodiment, the medical diagnostic apparatus 10 comprises an ultrasound machine 12 and associated measurement probe 14. Any suitable type of ultrasound machine 12 and measurement probe 14 may be used, for example any ultrasound machine 12 and transducer probe 14 that are configured to obtain ultrasound image data that is suitable for 3D imaging.

Although in the present embodiment the medical diagnostic apparatus 10 comprises an ultrasound machine 12, in other embodiments the medical diagnostic apparatus 10 may comprise an apparatus of an alternative modality. For example, the medical diagnostic apparatus may comprise a CT scanner, MR scanner, PET scanner or SPECT scanner.

The ultrasound machine 12 comprises a main display screen 16 for displaying a main ultrasound image, a control screen 18 for displaying control information, and a scanner console 20. In the present embodiment, the scanner console 20 comprises an input device or devices such as input buttons or knobs, rotary switches, a computer keyboard, a mouse or a trackball. In alternative embodiments, the control screen 18 is a touch screen, which is both a display device and a user input device. Further embodiments may comprise a control screen 18, display screen or main display screen 16 that does not form part of the ultrasound machine 12. The ultrasound machine 12 also comprises a data store 30 for storing volumetric data.

The ultrasound machine 12 comprises a processing apparatus 22 for processing of data, including image data. The processing apparatus 22 includes data receiving circuitry 24 for receiving data, lighting circuitry 26 for simulating lighting and rendering circuitry 28 for rendering images. In the present embodiment, the processing apparatus 22 also comprises segmentation circuitry 30 for performing segmentation and display control circuitry 32 for display of rendered images. In alternative embodiments the processing apparatus 22 may be part of any suitable medical diagnostic apparatus (for example a CT scanner or MR scanner) or other image processing apparatus (for example, a PC or workstation). The processing apparatus 22 may be configured to process any appropriate modality of volumetric data, for example ultrasound, CT, MR, PET or SPECT data.

In the present embodiment, the data receiving circuitry, lighting circuitry and rendering circuitry are each implemented in processing apparatus 22 by means of a computer program having computer-readable instructions that are executable to perform the method of the embodiment. However, in other embodiments the data receiving circuitry, lighting circuitry and rendering circuitry may each be implemented in software, hardware or any suitable combination of hardware and software. In some embodiments, the various circuitries may be implemented as one or more ASICs (application specific integrated circuits) or FPGAs (field programmable gate arrays).

The processing apparatus 22 also includes a hard drive and other components including RAM, ROM, a data bus, an operating system including various device drivers, and hardware devices including a graphics card. Such components are not shown in FIG. 2 for clarity.

The system of FIG. 2 is configured to perform two methods, which may be performed individually or in combination. The first method is described below with reference to FIGS. 3 and 4. The first method is a method of lighting a cavity using a virtual directional light source which is placed outside the cavity. The virtual directional light source casts light rays into the volume. Calculation of irradiance is suspended until the light rays enter the cavity, to allow the virtual directional light source to illuminate the cavity without all of the virtual light energy being absorbed before it reaches the cavity.

The second method is described below with reference to FIGS. 5 to 8d. The second method is a method of lighting a cavity using a virtual point light source which is placed inside the cavity. Irradiances resulting from the virtual point light source are adjusted so that there is a reduction in the difference in irradiance between points close to the virtual point light source and points further away from the virtual point light source. The adjustment in irradiance may lead to illumination of a greater part of the cavity than would be the case with an inverse-square-law fall-off in irradiance.

In the discussion of FIGS. 3 and 4 and FIGS. 5 to 8d below, the first method and second method are described separately. However, in some embodiments, both methods may be performed simultaneously on the same data. For example, for a given volumetric data set, a virtual directional light source to which the first method is applied may be placed outside a cavity, and a virtual point light source to which the second method is applied may be placed inside the cavity.

We turn first to the first method. The first method has a series of stages as illustrated in overview in the flowchart of FIG. 3.

Figure 3:
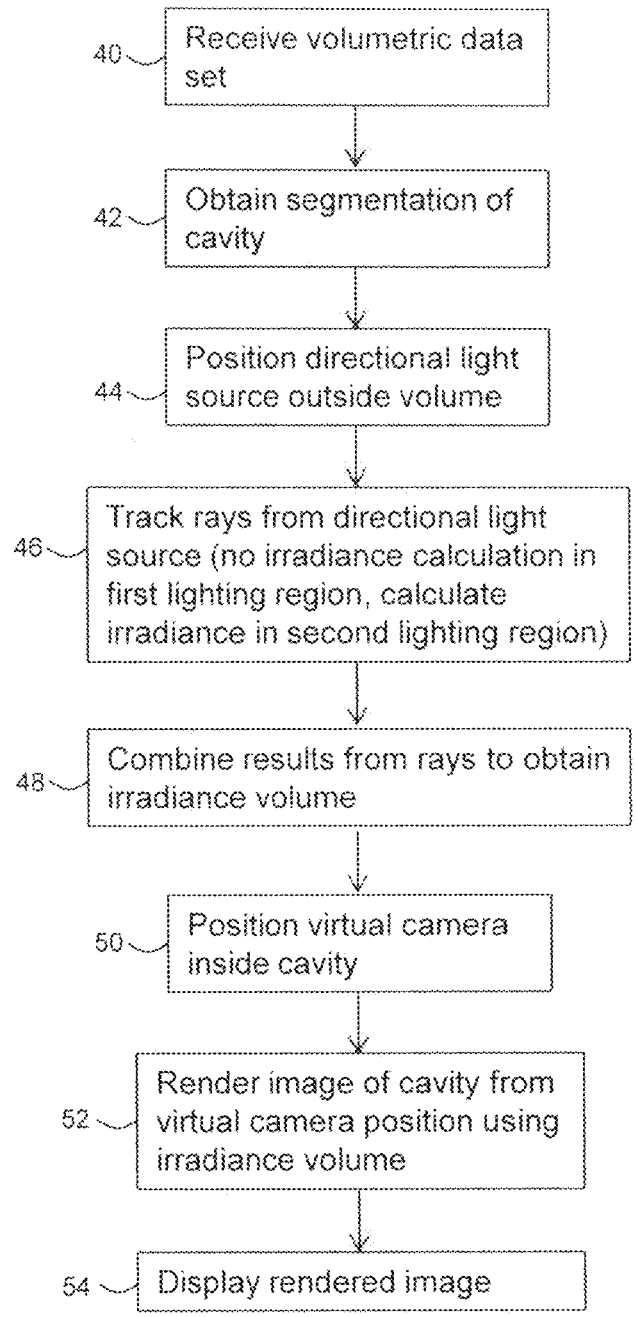
FIG. 3 is a flowchart illustrating in overview the process of an embodiment.

At stage 40 of FIG. 3, the data receiving circuitry 24 receives a volumetric imaging data set. In the present embodiment, the volumetric imaging data set has been obtained by reconstruction of raw ultrasound data, where the raw ultrasound data was obtained from ultrasonic transmission and reception to and from a three-dimensional region of a patient. In the present embodiment, the volumetric imaging data set is reconstructed from a scan that is currently in process. The data receiving circuitry 24 receives the volumetric imaging data set from another part of the processing apparatus 22. In other embodiments, the volumetric imaging data set is received from the data store 30 or from a remote data store.

The three-dimensional region of the patient includes a region of interest. In the present embodiment, the region of interest is a cavity, for example the gallbladder. In other embodiments, the region of interest may be any interior structure of the body, for example, any cavity, duct, vessel, lumen, airway, air-filled region or fluid-filled region. In some embodiments, the region of interest comprises an anatomical structure that may traditionally be viewed by endoscopy.

In the present embodiment, the volumetric imaging data set is obtained from an ultrasound scan. In alternative embodiments, the volumetric imaging data set may have been obtained using any appropriate imaging modality. In further embodiments, the volume imaging data set may comprise data that has not been obtained from a medical imaging scan, for example virtual anatomy data or polygon data that has not originated from a medical scan.

The volumetric imaging data set comprises an array of voxels. The array of voxels is representative of a three-dimensional volume, which corresponds to some or all of the three-dimensional region of the patient. Each voxel has a position in the coordinate space of the volumetric imaging data set and an associated signal intensity. In alternative embodiments, the volumetric imaging data set may comprise multiple channels of signal intensity. For example, more than one signal intensity channel may be used if the volumetric imaging data set comprises dual-energy CT data, if the volumetric imaging data set comprises both pre-contrast and post-contrast data, or if the volumetric imaging data set comprises data obtained in a multi-volume fusion scenario. In further embodiments, the volumetric imaging data set may comprise non-voxel-based data.

Different tissue types may be associated with different signal intensities. For example, in some cases, voxels that are representative of a fluid-filled cavity may have lower signal intensities than voxels that are representative of bone or soft tissue.

The volumetric imaging data set may contain a representation of materials, surfaces and so on that occur in the subject. In the discussion below (with reference to all embodiments), lighting processes may be referred to as if they occurred in a physical space. However, we are usually describing virtual (simulated) processes occurring as numerical operations on a volumetric imaging data set. Similarly, when we discuss the volumetric imaging data set as if it were a physical space having a physical extent, we are generally referring to the coordinate space that is represented by the voxels of the volumetric imaging data set.

At stage 42, the segmentation circuitry 30 obtains a segmentation of the cavity in the volumetric imaging data set. In the present embodiment, the segmentation circuitry 30 obtains a segmentation of the cavity by applying an intensity threshold to the volumetric imaging data set. The segmentation circuitry 30 classifies voxels having an intensity below the intensity threshold as part of the cavity. The segmentation circuitry 30 may also perform further operations, for example morphological operations, in obtaining the segmentation of the cavity. The segmentation provides information on the extent of the cavity. The segmentation circuitry 30 may also obtain a segmentation of further anatomical structures.

If a threshold is used to identify the boundaries of the cavity then the area identified by the threshold may also include the outside of the body. However, areas on the outside of the body may be ignored in subsequent processing.

In other embodiments, any suitable segmentation process for obtaining a segmentation of the structure of interest may be used. For example, the segmentation process may comprise thresholding, region growing, an edge detection method, a flood fill segmentation, an atlas-based segmentation or a level-set method. The segmentation process used may depend on the type of anatomical structure being detected. For example, in some embodiments in which the anatomical structure of interest is an artery, a segmentation process that comprises vessel tracking may be used. In some embodiments, a contrast medium may be used to create image contrast that may be used in the segmentation. In one embodiment, the segmentation is obtained by performing a flood fill starting at the position of a virtual camera.

At stage 44, the lighting circuitry 26 places a virtual directional light source outside the volume that is represented by the volumetric imaging data set. In the present embodiment, the lighting circuitry 26 places the directional light source in accordance with input from a user (for example, a clinician or a radiologist). The user may specify the direction of the directional light source using any suitable input device, for example a trackball or other controls on scanner console 20. In other embodiments, the lighting circuitry 26 may position the directional light source automatically. In some embodiments, multiple directional light sources are positioned by lighting circuitry 26.

In the present embodiment, the lighting circuitry 26 also places a virtual point light source inside the cavity. The lighting circuitry 26 determines the position of the point light source in accordance with input from the user. In other embodiments, the lighting circuitry 26 determines the position of the point light source automatically. In other embodiments, no virtual point light source is used.

At stage 46, the lighting circuitry 26 simulates light from the directional light source using a lighting simulation process. The lighting simulation process comprises casting rays from the direction of the directional light source through the volume. The lighting circuitry 26 applies the lighting simulation process differently for a first lighting region than for a second lighting region.

The lighting circuitry 26 uses the segmentation to locate the boundary of the cavity, e.g. the position of a wall of the cavity. The lighting circuitry 26 defines a first lighting region including a part of the volume that lies between the directional light source and the cavity. In the present embodiment, the first lighting region also includes a part of the cavity that borders the wall of the cavity that is nearest to the directional light source. The lighting circuitry 26 defines a second lighting region including a part of the cavity.

In the present embodiment, the application of the lighting simulation process differs between the first and second lighting region in that the lighting circuitry 26 does not calculate any depositing of virtual light energy from rays when the rays are passing through the first lighting region. The lighting circuitry 26 calculates a depositing of virtual light energy once the rays enter the second lighting region.

An exemplary lighting simulation process is described in more detail below with reference to FIG. 4.

Figure 4:
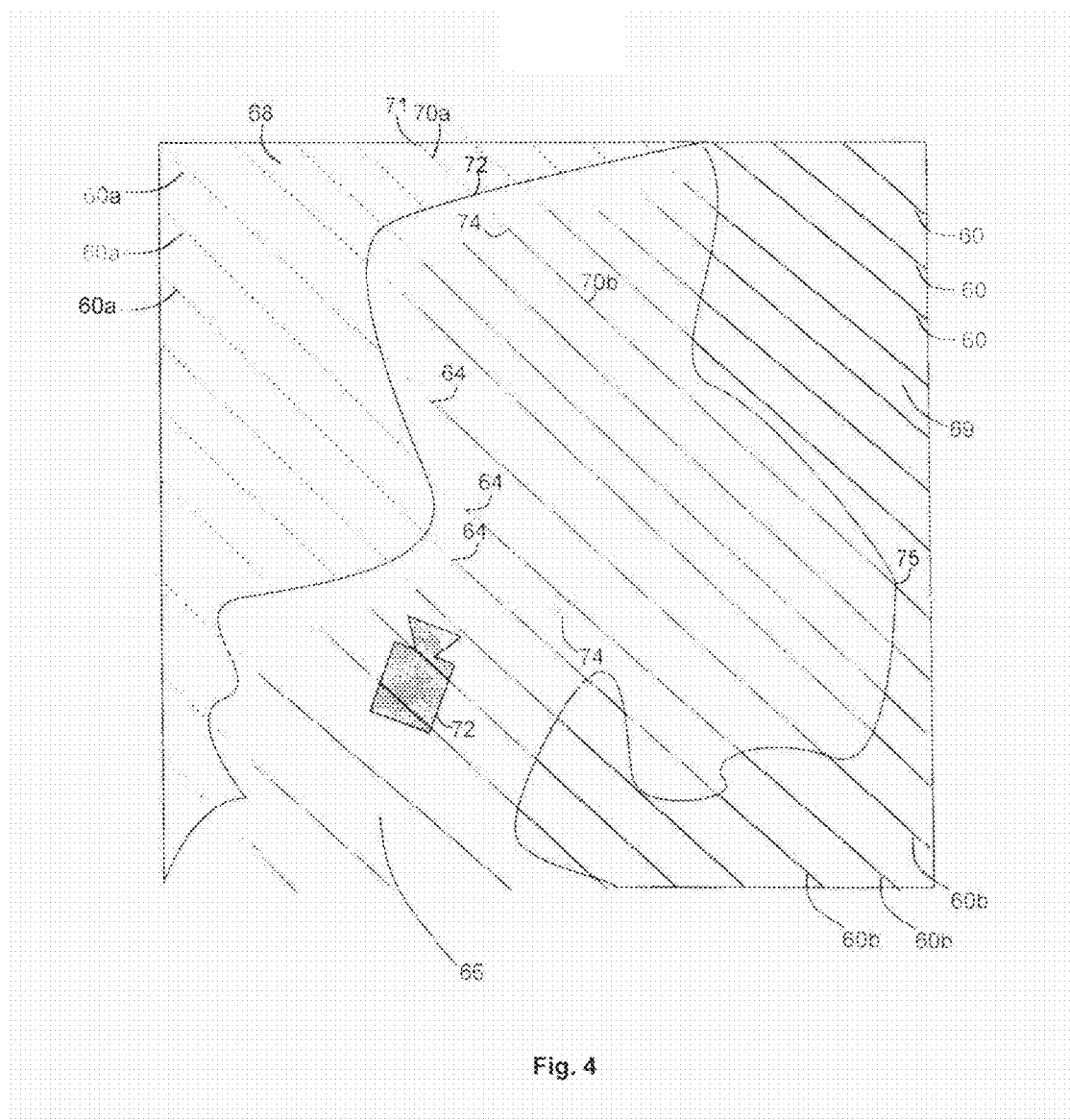
FIG. 4 is a schematic diagram illustrating directional lighting of a cavity.

FIG. 4 shows a plurality of parallel rays 60 issuing from a virtual directional light source. A directional light source may be a simulated light source that provides parallel light issuing from a particular angle with respect to the volume. A directional light source may be positioned in space, in that rays from the directional light source may begin on a particular plane with respect to the volume. In the example of FIG. 4, the directional light source is positioned such that the parallel rays begin outside the volume on the upper left of FIG. 4.

Some of the parallel rays 60 pass through a cavity 66. Rays that pass through the cavity 66 as depicted as comprising a first portion 60a indicated by a dotted line and a second portion 60b indicated by a solid line. The first portion 60a may be considered to be the part of the ray that is included in the first lighting region and the second portion 60b may be considered to be the part of the ray that is included in the second lighting region. The boundary between the first portion 60a and second portion 60b occurs at transition point 64. In the illustrated embodiment, the first portion 60a and second portion 60b, corresponding to first and second lighting regions, are contiguous.

In the present embodiment, only rays that pass through the cavity 66 are considered in the calculation of virtual light energy. In other embodiments, a calculation may also be performed for rays that do not pass through the cavity 66. The calculation performed for rays that pass through the cavity 66 is described below.

Each ray enters the volume from the direction of the directional light source. In the present embodiment, the first portion 60a of each ray does not distribute any light energy into the volume. The ray starts to distribute virtual light energy into the volume on arrival at transition point 64 on the ray. Transition point 64 is inside the cavity (as determined by the segmentation). Transition point 64 is offset from the cavity wall by a given distance. Virtual light energy is absorbed as the second portion 60b of the ray passes through the volume. As the ray progresses, the amount of virtual light energy absorbed is computed and when a sufficient portion of the virtual light energy is absorbed then the traversal of the ray is terminated.

In the present embodiment, the transition points 64 are all offset from the cavity wall by the same offset distance. The offset distance is a constant distance which is stored in lighting circuitry 26. In some embodiments, the offset distance may be set by a user. In other embodiments, the offset distance may be automatically determined by the lighting circuitry 26. For example, the offset distance may be obtained based on the segmentation of the cavity. In some embodiments, the offset distance may be a proportion of a size of the cavity.

In some embodiments, the offset distance may vary for different rays. For example, the offset distance at one part of the cavity may be different from the offset distance at another part of the cavity. In some embodiments, no offset is used. In such embodiments, the ray may start to distribute virtual light energy as soon as it enters the cavity. In such embodiments, the second lighting region may comprise the entire cavity.

We consider one exemplary ray's traversal in more detail. The ray is indicated on FIG. 4 by numerals 70a and 70b. The ray enters the volume at point 71. The ray passes through a region 68 of the volume. Region 68 is a region that lies between the directional light source and the cavity. Region 68 may represent, for example, bone and/or soft tissue. In physical terms, the material that is represented by region 68 may be expected to absorb light. However, in the method of FIG. 3, no virtual light energy is absorbed by region 68.

The ray enters the cavity at point 72. The ray continues through a part of the cavity adjacent to the cavity wall, and arrives at transition point 74. No virtual light energy is absorbed between point 72 and transition point 74. Transition point 74 is offset from point 72 by a fixed distance. Transition point 74 is therefore spaced away from the wall of the cavity.

At transition point 74, the ray begins to distribute virtual light energy into the volume. The lighting circuitry 26 calculates irradiance due to the ray at each of plurality of sample points along the second portion 70b of the ray. In the present embodiment, the sample points are equally spaced along the second portion 70b of the ray. Any suitable spacing may be used. The irradiance at each sample point is a product of the virtual light energy of the ray when it reaches the sample point and an absorption function at the sample point.

In the present embodiment, the absorption function is assigned to each sample point in dependence on the intensities of voxels neighboring that sample point. For example, an intensity may be determined for a sample point by interpolating intensities from neighboring voxels, and an absorption function may be assigned in dependence on the determined intensity. High voxel intensity may be associated with high absorption. In another embodiment, an absorption function may be assigned to each voxel in dependence on the voxel's intensity, and an absorption function for a sample point may be determined by interpolating absorption functions from neighboring voxels.

In some embodiments, voxels are classified as belonging to particular objects (for example, particular anatomical features) and the absorption function at each sample point is determined in dependence on the classification of the neighboring voxels. Different optical properties may be assigned to different objects. In some embodiments, the segmentation of the cavity is used to classify some voxels as part of the cavity, and voxels that are classified as part of the cavity are assigned a particular absorption function.

In the present embodiment, the absorption function is a function having color-dependent absorption properties, and may be described as a spectral absorption. The absorption function is defined such that blue and green light are absorbed more strongly than red light, to represent the absorption of tissue. The irradiance calculated at each sample point is a spectral irradiance, which may be described as a combination of red, green and blue components $I_r$, $I_g$ and $I_b$ (or more generally may be described as irradiance per wavelength for the full spectrum of relevant wavelengths). In other embodiments, the irradiance may not be a spectral irradiance.

In the present embodiment, the calculated irradiance is not a directional irradiance. In other embodiments, an associated irradiance direction may be determined at each sample point for which irradiance is calculated. The irradiance direction may be the direction of incidence of light received at each sample point. A model for irradiance may describe an irradiance field in six dimensions, $I(x,y,z,\lambda,\theta,\phi)$ where $\lambda$ is the wavelength and $\theta$, $\phi$ represents the incoming angle of the irradiance energy. However, a datastructure of this dimensionality may not be practical in some implementations. Any suitable irradiance model may be used.

For each of the plurality of sample points on the ray for which irradiance is calculated, the lighting circuitry 26 distributes irradiance to a plurality of neighboring voxels using any appropriate method. In the present embodiment, the irradiance is distributed to the eight nearest neighbor voxels. Distributing to eight nearest neighbors may be considered to be analogous to trilinear interpolation. In other embodiments, the irradiance at each sample point may be distributed to any appropriate number of voxels.

As the ray passes through the cavity, some of the virtual light energy is absorbed at each sample point and the ray becomes weaker and redder. Once a sufficient portion of the virtual light energy in the ray has been absorbed, no further calculations may be performed on the ray. In the present embodiment, if 99% of the virtual light energy in the ray has been absorbed, no further calculations are performed on that ray. In other embodiments, the portion may be different, for example 90% or 95%.

If there is enough light energy remaining such that the ray has not yet been terminated, the ray enters a further region 69 of the volume at point 75. The lighting circuitry 26 performs irradiance calculations at sample points on the second portion of the ray 70b that lie within the further region 69 until, say, 99% of the virtual light energy has been absorbed, or until the ray exits the volume.

In the present embodiment, although calculation of absorption is suspended when passing through the region 68 which lies between the virtual directional light source and the cavity, calculation of absorption is not suspended when a ray enters region 69 which is on the other side of the cavity from the virtual light source. In other embodiments, calculation of absorption may be suspended in both region 68 and region 69. In some circumstances, region 68 and region 69 may comprise similar tissue. In the present embodiment, no absorption is calculated for rays that do not pass through the cavity 66. In other embodiments, absorption may be calculated for rays that do not pass through the cavity 66.

In the present embodiment, region 68 comprises all of the part of the volume that lies between the directional light source (which is outside the volume) and the cavity. In other embodiments, a region for which calculation of irradiance is suspended, or for which absorption is reduced, may comprise only a particular part of the volume outside the cavity, for example a particular anatomical structure, or regions having intensity above a given value.

In the present embodiment, only one cavity is present in the volume. In some volumes, multiple cavities may exist. In some such cases, the calculation of irradiance may be suspended for all cavities except for the cavity in which the camera is placed. In some embodiments, multiple cavities may be separated by very thin material and/or by material which has been attributed a reasonably high transparency. In some circumstances in which the cavities are separated by thin and/or transparent material, multiple distinct cavities may be treated as a single cavity and the calculation of irradiance may performed throughout most or all of the space occupied by the multiple cavities. The light interaction in the multiple cavities may give visual hints about the spatial relationship between the multiple cavities.

In the present embodiment, no calculation of irradiance is performed for the first portion 60a of each ray (which is in the first lighting region). In a further embodiment, the lighting circuitry 26 calculates irradiances for sample points in the first portion 60a of each ray, but the lighting circuitry 26 modifies the absorption function associated with sample points on the first portion, for example sample points that lie within region 68.

For example, in an embodiment, the lighting circuitry 26 determines the absorption at a given sample point using the intensities of the surrounding voxels. The lighting circuitry 26 then reduces the absorption at that sample point to a small proportion of the original absorption, for example to 1% of the original absorption. The lighting circuitry 26 calculates irradiance for each sample point in the first portion 60a using the reduced absorptions.

In the present embodiment, no calculation of irradiance is performed for the first portion 60a of each ray (the first lighting region) and a full calculation of irradiance is performed for the second portion 60b of each ray (the second lighting region). The first portion and second portion meet at transition point 64.

In other embodiments, there is a transition region between the first lighting region and the second lighting region. In the transition region, there is a gradual transition between the lighting simulation process applied in the first lighting region and the lighting simulation process applied in the second lighting region. In some embodiments, no irradiance is calculated in the first portion 60a of each ray. The ray then enters the transition region, and a reduced irradiance is calculated while the ray is in the transition region. For example, sample points in the transition region may be assigned a reduced absorption. The absorption may be gradually increased between the point at which the ray enters the transition region and the point at which the ray exits the transition region. The gradual increase may be such that at the point at which the ray exits the transition region and enters the second lighting region, there is no reduction in absorption.

In another embodiment, the lighting circuitry 26 calculates irradiances for sample points in the first portion 60a of each ray without reducing the absorption. When each ray reaches the transition point 64, within the cavity, the lighting circuitry 26 increases the virtual light energy associated with the ray to its starting value, or to a proportion of its starting value, for example to 90% of its starting value. In some such embodiments, the lighting circuitry 26 does not stop the calculation of a ray when a given proportion (for example, 99%) of the virtual light energy is absorbed.

In the present embodiment, the lighting simulation process of stage 46 simulates scattering as well as direct illumination. At some sample points on a ray, scattering may occur rather than absorption. In the present embodiment, only single scattering is taken into account. In some embodiments, multiple scattering may be taken into account. In some embodiments, reflection may also be taken into account.

The lighting circuitry 26 also calculates irradiance from the virtual point light source 74 by casting rays from the point light source 74 and determining irradiance for each of a plurality of sample points along each ray in dependence on an absorption function at that sample point. The irradiance at each sample point is distributed to neighboring voxels as described above. In the present embodiment, irradiance from the point light source 74 is calculated without reducing or eliminating absorption at any part of the ray. For rays that are emitted by the point light source 74, the lighting simulation process is applied in the same way for all parts of the volume. In other embodiments, the lighting simulation of the rays from the point light source 74 may be applied differently for a first and second lighting region, which may or may not be the same as the first and second lighting region for the directional light source.

At stage 48, the lighting circuitry 26 combines the lighting simulation results from rays from the directional light source and from the point light source to obtain an irradiance volume. In the irradiance volume, each voxel has an associated irradiance which may be a combination of irradiance contributions from a plurality of rays that have deposited virtual light energy at sample points near the voxel.

In the present embodiment, the irradiance volume comprises at least one irradiance value for each voxel position in the volumetric imaging data set. In other embodiments, the irradiance volume may be defined for a grid of reference points which may or may not be coincident with voxels. In some embodiment, the irradiance volume may be defined for a downsampled grid of voxels. In further embodiments, the irradiance volume may be defined for a set of points that do not form a grid, for example a point cloud, a tree structure, or a tree structured point cloud.

In the present embodiment, a global illumination lighting model is used to calculate irradiance at stages 46 and 48. In other embodiments, any suitable lighting model may be used.

At stage 50, the rendering circuitry 28 positions a virtual camera 72 within the cavity 66. The virtual camera is representative of a viewing position and orientation. In the present embodiment, the rendering circuitry 28 positions the virtual camera in accordance with an input from a user (for example, a clinician or radiologist). The user may specify the position and orientation of the virtual camera 72 using any suitable input device. In alternative embodiments, the rendering circuitry 28 may position the virtual camera 72 automatically.

At stage 52, the rendering circuitry 28 renders an image based on the irradiance volume. In the rendering, the rendering circuitry 28 refers both to the irradiance volume and to the volumetric imaging data set. The input to the rendering circuitry 28 on which the rendering is based may also include the segmentation and/or other data sets, for example clipping structures.

The image is rendered as if viewed from the virtual camera. The rendering circuitry 28 casts rays from the camera into the volume represented by the volumetric imaging data set. Each ray may correspond to a pixel of a two-dimensional image data set that is to be obtained by the rendering of stage 52. Each ray from the camera steps through the volume represented by the volumetric imaging data set in increments of the voxel spacing. In other embodiments, a different spacing may be used.

For a given ray that is cast from the camera, the rendering circuitry 28 determines irradiance at each of a series of incremental points along the ray. If an incremental point is representative of empty space the ray skips on to the next incremental point.

The rendering circuitry 28 determines irradiance at each incremental point by interpolating irradiance from neighboring voxels of the irradiance volume. In the present embodiment eight nearest-neighbor voxels are considered in the interpolation for each point. In other embodiments, a different number of voxels may be considered. The rendering circuitry 28 integrates the irradiances at each incremental point along a ray from the camera to obtain a pixel color value for the ray. The rendering circuitry 28 thereby determines a color value for each pixel in the two-dimensional image data set.

At stage 54, the display control circuitry 32 displays an image corresponding to the two-dimensional image data set on main display screen 16. The displayed image is an image of the cavity as illuminated by both the directional light source and the point light source 74.

By suspending or reducing the irradiance contribution until light from the directional light source enters the interior structure of interest (for example, a cavity of interest), directional lighting of an interior structure may be obtained. If the irradiance contribution were not suspended or reduced, it may be expected that light from a directional light source placed outside the volume would not reach the interior structure. The virtual directional light source may serve as a form of fill light in the image of the interior structure.

The application of the lighting simulation process (for example, the reduction or elimination of absorption until each ray is inside the interior structure) may ensure that at least some light from the directional light source reaches the interior structure. The application of the lighting simulation process may ensure that a desired light level is achieved inside the interior structure.

The position of the directional light source and/or details of the lighting simulation process may be selected such that the directional light source illuminates at least one selected part of the interior structure, for example a part of the wall of a cavity.

The fill lighting provided by the directional light source may mitigate some effects of the point light source. For example, the point light source may cast harsh shadows, which may be made less harsh by the presence of the fill lighting from the directional light source. The point light source may provide strong illumination near to the point light source, and may not illuminate parts of the interior structure that are further from the point light source. The fill lighting from the directional light source may illuminate parts of the interior structure that are not adequately illuminated by the point light source.

In some embodiments in which the calculation of irradiance starts as soon as the ray enters the interior structure, the wall of the interior structure at which the ray enters may appear very bright in the resulting image. By starting the calculation of irradiance at a transition point 64 that is positioned away from the wall of the interior structure by an offset distance, it may be possible to avoid the wall of the interior structure looking too bright. The offset distance may be chosen to provide an aesthetically pleasing effect. The offset distance may be chosen to provide a good image of the interior structure, for example an image that it is easy for a clinician to interpret.

In some embodiments, more than one virtual directional light source is placed by the lighting circuitry 26 at stage 42. The lighting circuitry 26 simulates light for each of the virtual directional light sources. For each of the directional light sources, the lighting circuitry determines a first lighting region and a second lighting region. The first lighting region may comprise a region that is between the directional light source and the cavity. The first lighting region may also comprise a part of the cavity that is adjacent to the wall of the cavity that is nearest the directional light source. The second lighting region may comprise the remainder of the cavity. For each directional light source, the lighting circuitry 26 applies the lighting simulation process differently for the respective first region than for the respective second region. The lighting circuitry casts a plurality of rays from each of the directional light sources, determines irradiance at each of the plurality of sample points along each ray, and distributes the irradiance to voxel positions. Each voxel may receive irradiance contributions from multiple directional light sources.

In some embodiments, directional light sources may be placed on opposite sides of the volume. Directional light sources may be placed at a predetermined angle to each other. For example, directional light sources may be placed opposite to each other. Using more than one directional light source may avoid harsh shadowing that may in some circumstances result from using a single directional light source.

In some embodiments, each of the directional light sources emits the same amount of virtual light energy. In other embodiments, one of the directional light sources may emit more virtual light energy (and so may provide brighter illumination) than another of the directional light sources. In some circumstances, the illumination of an interior structure by a pair of equally bright directional light sources arranged in opposite directions may result in a dark line between the areas illuminated by the directional light sources. By setting one light to be brighter than the other, the dark line may be reduced. In some circumstances, a more aesthetically pleasing lighting effect and/or an image that is easier to interpret may be produced by using directional light sources of different brightness. The illumination produced by lights of different brightness may appear more natural than that produced by lights of equal brightness.

In some embodiments, the lighting circuitry 26 places one or more virtual directional light sources or other virtual light sources and the rendering circuitry 28 renders an initial image of an interior structure. The user adjusts one or more lighting parameters using input controls, for example using a trackball, rotary switches, a mouse or a keyboard. For example, the user may adjust the position of a virtual light source or the direction of illumination if the light source is directional. The user may adjust the brightness of a light source. The user may adjust the relative brightness of two or more light sources. In some embodiments, the user may adjust the offset distance at which the irradiance calculation begins. The user may select or modify the extent of the first lighting region, second lighting region and/or transition region. The user may select or modify the application of the lighting simulation process in one or more regions. For example, the user may determine an extent to which absorption is reduced in the first lighting region. The user may determine how gradually absorption is changed in the transition region. The rendering circuitry 28 renders one or more further images with new parameters that have been set by the user.

In some embodiments, parameters of the light sources are individually controllable. In some embodiments, the user may adjust parameters for more than one light source at once. For example, the user may operate a single control to adjust the position of all the light sources or to reduce the brightness of all the light sources. The controls offered to the sonographer may be made simpler by limiting the parameters that may be adjusted.

In the above embodiments, a lighting simulation process which simulates light from a directional light source is applied differently for a region between a directional light source and a cavity than within the cavity itself. In further embodiments, a lighting simulation process which simulates light from a virtual point light source, or from any other virtual light source, may be applied differently for a first region than a second region. The second region may be a region of interest (for example, a cavity) and the first region may be a part of the volume that is outside the region of interest (for example, tissue surrounding a cavity).

For example, in one embodiment, a virtual point light source is placed outside a volume and rays are cast from the point light source into the volume. The calculation of irradiance is suspended until the rays from the point light source have entered the cavity. In another embodiment, a virtual point light source is placed inside the volume, but outside the cavity. Rays are cast from the point light source into the cavity. The calculation of irradiance is suspended until the rays from the point light source have entered the cavity.

We turn now to a second set of embodiments relating to a second method which may be performed by the system of FIG. 2, in which a virtual point light source is placed within a cavity and irradiances resulting from the virtual point light source are adjusted to modify the fall-off in irradiance with distance from the virtual point light source. The second method is described with reference to FIGS. 5 to 8*d*. The second method has a series of stages as illustrated in overview in the flowchart of FIG. 5.

Figure 5:
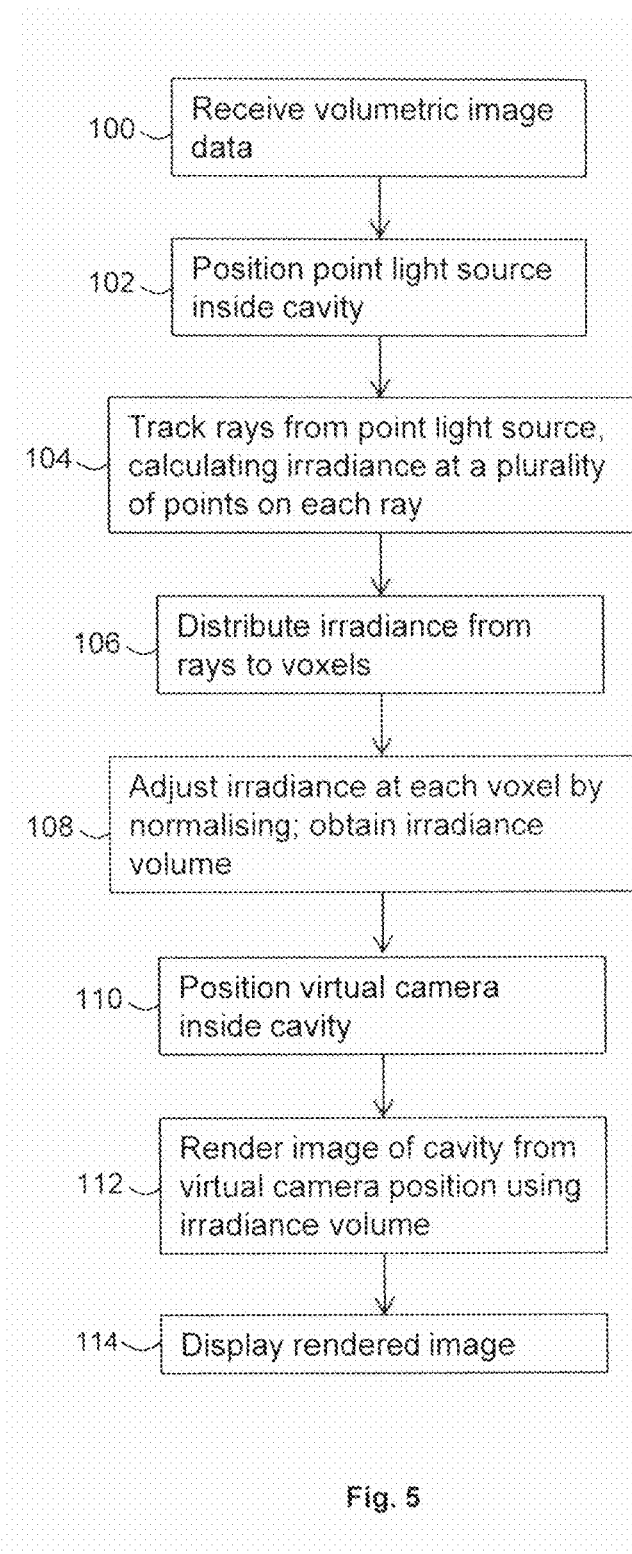
FIG. 5 is a flowchart illustrating in overview the process of an embodiment.

The apparatus illustrated in FIG. 2 is capable of performing both the process of FIG. 3 and the process of FIG. 5. However, in other embodiments, an apparatus may be configured to perform the process of FIG. 5 and not the process of FIG. 3, or to perform the process of FIG. 3 and not the process of FIG. 5.

At stage 100 of FIG. 5, the data receiving circuitry 24 receives a volumetric imaging data set. In the present embodiment, the volumetric imaging data set has been obtained by reconstruction of raw ultrasound data. In other embodiments, any appropriate modality may be used. The volumetric imaging data set comprises an array of voxels.

The array of voxels is representative of a three-dimensional volume, which corresponds to some or all of the three-dimensional region of the patient. Each voxel has a position in the coordinate space of the volumetric imaging data set and an associated signal intensity.

In the present embodiment, the three-dimensional region of the patient includes a region of interest which comprises a cavity. In other embodiments, the region of interest may comprise any interior structure of the body, for example a duct, vessel, lumen, airway, air-filled structure or fluid-filled structure.

At stage 102, the lighting circuitry 26 places a virtual point light source 120 inside the cavity. In the present embodiment, the position of the virtual point light source 120 is selected by a user using any appropriate input device. In other embodiments, the lighting circuitry 26 determines a position for the virtual point light source 120 automatically. In some embodiments, the lighting circuitry 26 receives a segmentation of the cavity from the segmentation circuitry 40 and determines a position for the point light source 120 based on the segmentation.

Stages 104 to 106 may be considered to form the first pass of a two-pass process, and stages 110 to 114 may be considered to form the second pass of the two-part process. The first pass applies a lighting simulation process to create an irradiance volume, and the second pass uses the irradiance volume to render an image for display.

At stage 104, the lighting circuitry 26 casts light into the volume by tracking a plurality of rays from the point light source 120 into the volume, and calculates irradiance at a plurality of points on each ray. The irradiance may for example be expressed in $W/m^3$, in any other suitable units, or as an uncalibrated value.

The tracking of the plurality of rays comprises simulating the emission of a large plurality of rays from the virtual point light source 120. In the present embodiment, the emission of rays is treated stochastically. Stochastic emission of rays may also be called random emission. The rays are emitted by a stochastic process such that, on average, an equal number of rays is emitted in each unit of solid angle. Stochastic emission may be more straightforward to implement than an equal sampling over a sphere in which the virtual point light source 120 is centered. In other embodiments, rays may be omitted at equal angular intervals, or using any other suitable distribution of the rays in space. More than one ray may be emitted at each given angle.

Although the term rays is used in this description, the rays may be considered as virtual photons. However, the behavior of the virtual photons may be different from that expected of real photons. In some circumstances, a part of the energy of a virtual photon may be absorbed and the virtual photon may continue after the absorption of the part of the energy. In some circumstances the virtual photon may lose energy without changing direction.

Figure 6:
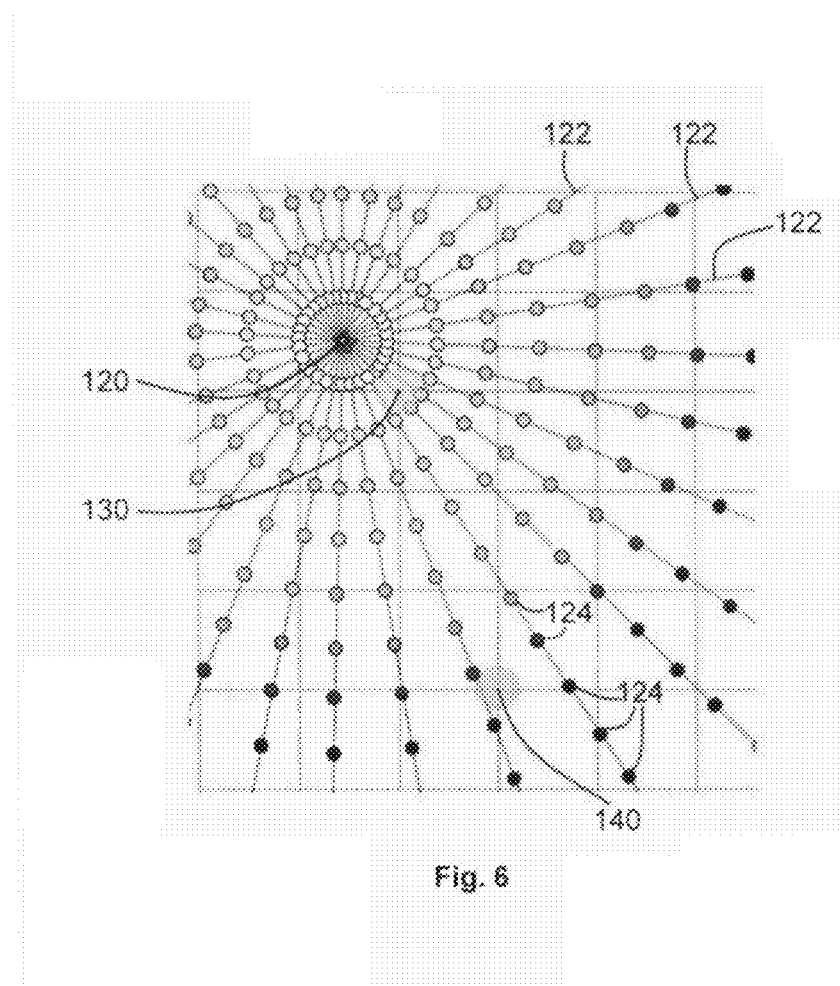
FIG. 6 is a schematic diagram of virtual photons issuing from a virtual point source.

FIG. 6 is a schematic diagram which is representative of a slice through the three-dimensional volume. FIG. 6 shows rays being emitted from a virtual point light source 120. For the purposes of the diagram, the rays 122 are shown as being approximately equally spaced in angle in two dimensions (although in the present embodiment the rays 122 are emitted stochastically in three dimensions). In FIG. 6, the point light source 120 is placed at the center of a small circular cavity with a soft translucent boundary layer.

For each of the rays 122, irradiance is calculated at each of a plurality of sample points 124, represented by circles in FIG. 6. In the present embodiment, the sample points are spaced equally along the ray, and the distance between sample points is the same for all rays. The irradiance is a spectral irradiance comprising red, green and blue components, $I_r$, $I_g$, and $I_b$. The irradiance at each sample point 124 is a product of the virtual light energy of the ray 122 when it reaches the sample point 124 and an absorption function at the sample point 124. The virtual light energy of a ray may be a measure of how much that ray contributes to irradiance. A ray with high virtual light energy may provide a greater irradiance than a ray with lower virtual light energy.

The virtual light energy comprises red, green and blue components. The absorption function is different for each of the red, green and blue components. In the present embodiment, the absorption function at each sample point 124 is determined in dependence on the intensity of voxels neighboring the sample point 124. Voxels neighboring the sample point 124 may be voxels in the neighborhood of the sample point 124. Voxels neighboring the sample point may comprise nearest-neighbor voxels, next-to-nearest neighbor voxels and/or a larger group of voxels near the sample point 124, for example voxels within a given distance of sample point 124. In some embodiments, voxels are classified as belonging to particular objects (for example, particular anatomical features), and the absorption function at each sample point is determined in dependence on the classification of the neighboring voxels. Different optical properties may be assigned to different objects.

In the present embodiment, a global illumination lighting model is used to calculate irradiances at stage 104. In global illumination, a lighting model may be used that includes both direct illumination by light coming directly from a light source and indirect illumination, for example illumination by light that has been scattered from another surface. In other embodiments, any suitable lighting model may be used. The calculation of irradiance at the sample points 124 comprises a photon mapping process that computes the absorption in discrete steps.

As the distance from the virtual point light source 120 increases, the amount of virtual light energy in each ray 122 decreases due to absorption. In FIG. 6, the decrease in the amount of virtual light energy for successive sample points 124 along a ray is illustrated by the circles representing the sample points 124 becoming darker.

Figure 1:
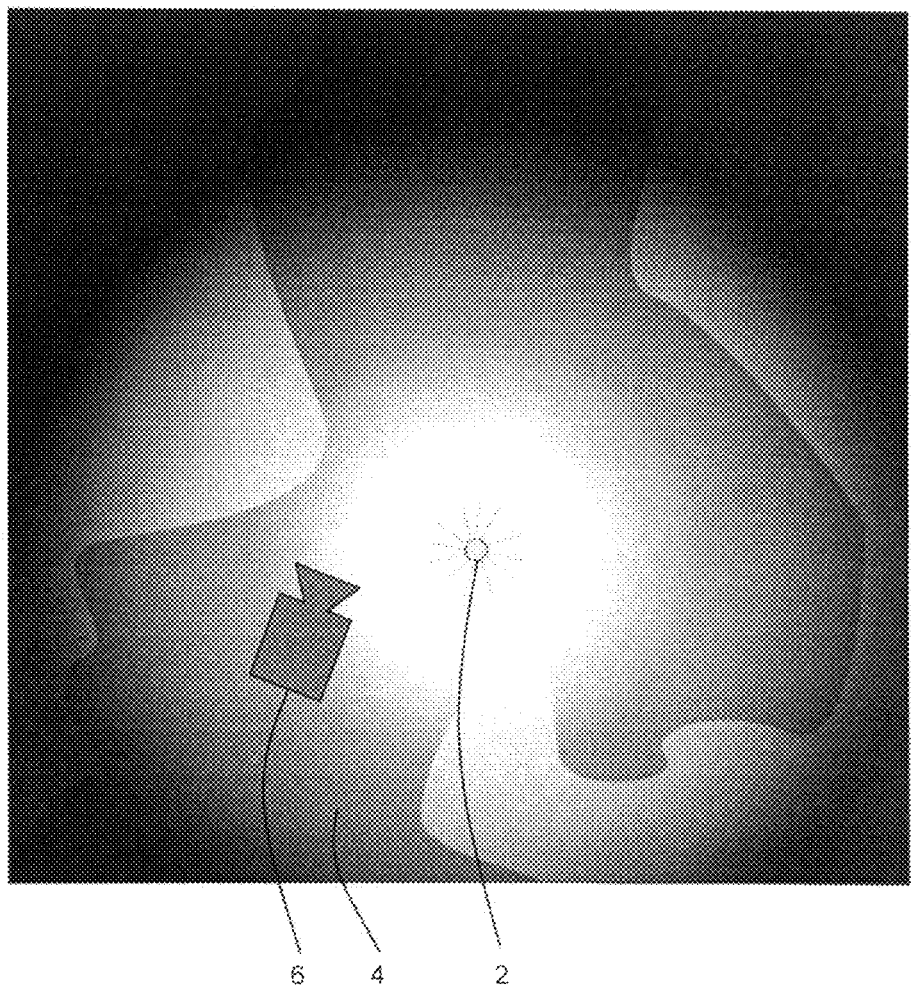
FIG. 1 is a schematic diagram of a cavity to be imaged, showing a virtual light source and virtual camera.

Furthermore, the rays 122 become further apart as the distance from the point light source 120 decreases. The number of rays passing through a given unit of surface area decreases in accordance with the inverse-square law, which causes the sharp fall-off in intensity seen in, for example, FIG. 1.

Figure 7A:
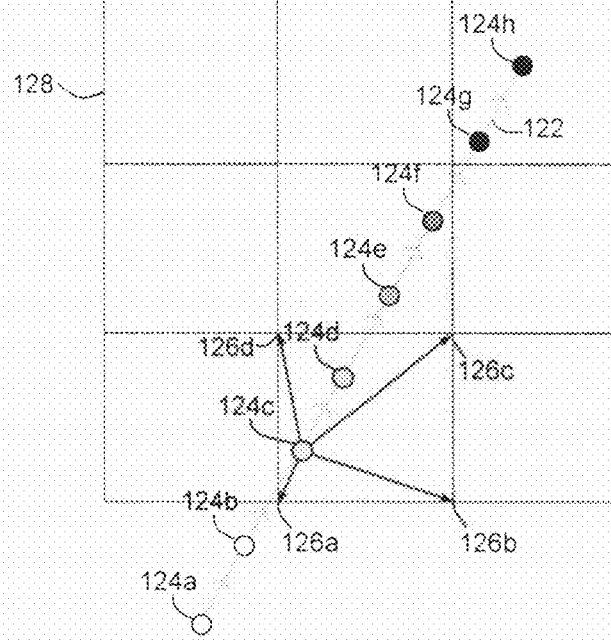
FIG. 7a is a schematic diagram of a ray passing through a volume.

FIG. 7a is a schematic diagram that is representative of part of a slice through the three-dimensional volume. FIG. 7a illustrates an example of a ray 122 (which may be considered to be a virtual photon) traversing the volume in a series of steps. The ray loses virtual light energy by absorption at each step. The ray may be terminated when a given proportion of the virtual light energy of the ray has been lost, for example when 99% of the virtual light energy of the ray has been lost.

The array of voxels in the volume is represented by the grid 128 of FIG. 7a (where voxels are located at the corners of the grid). Although only a slice of the volume voxel grid is represented in FIG. 7a, the volume voxel grid should be considered as a three-dimensional grid that extends through the volume.

At each of a plurality of sample points 124a to 124h, a part of the virtual light energy of the ray 122 is absorbed and irradiance is calculated based on the absorption. The irradiance comprises red, green and blue components, $I_r$, $I_g$, and $I_b$. As the ray 122 progresses in the direction of the arrows connecting the sample points, the virtual light energy in the ray 122 decreases, and the light becomes redder as blue and green light are preferentially absorbed according to the absorption function used in this embodiment. Any other desired absorption function may be used in other embodiments. Considering a given sample point 124c, irradiance is calculated for sample point 124c based on the amount of virtual light energy remaining in ray 122 when it reaches sample point 124c and on the absorption function at sample point 124c.

The calculation of irradiance is performed for each of the sample points 124 on each of the simulated rays 122. In the present embodiment, the irradiance is a spectral irradiance, but in other embodiments the irradiance may not be a spectral irradiance. In the present embodiment, the irradiance is not directional but in other embodiments the irradiance may be directional.

At stage 106, for each sample point, the lighting circuitry 26 distributes the irradiance at that sample point 124 to at least some of an array of reference points in the volume. In the present embodiment, the array of reference points corresponds to the array of voxels. Each reference point in this embodiment is coincident with a voxel center. The lighting circuitry 26 distributes the irradiance at each sample point 124 to voxels in the neighborhood of that sample point. In other embodiments, the reference points are points that do not correspond to voxels. In some embodiments, the array of reference points is a downsampled array of voxels.

Any suitable method may be used to distribute irradiance from a sample point to voxels in the neighborhood of the sample point. Distributing the irradiance from each sample point may be considered to be the reverse of interpolation. Therefore particular methods of distribution may be analogous to particular methods of interpolation.

In the present embodiment, for each sample point 124, the lighting circuitry 26 distributes the irradiance to the eight nearest-neighbor voxels to the sample point 124. Distributing to eight nearest-neighbor voxels may be considered to be analogous to trilinear interpolation. In other embodiments, the lighting circuitry 26 distributes the irradiance to a wider group of voxels than the eight nearest-neighbor voxels.

The lighting circuitry 26 distributes the irradiance from each sample point to the eight nearest-neighbor voxels by calculating a contribution weight for each of the eight nearest-neighbor voxels based on the distance between the sample point and the voxel. The lighting circuitry 26 then distributes irradiance to each of the eight nearest-neighbor voxels. The distributed irradiance at each of the eight nearest-neighbor voxels is equal to the irradiance at the sample point multiplied by the contribution weight for that voxel. In the present embodiment, the contribution weight is a dimensionless number between 0 and 1. The contribution weights for the eight nearest-neighbor voxels for a given sample point add up to 1. In other embodiments, the contribution weight may take different numerical values.

Considering the ray 122 of FIG. 7a, the irradiance at sample point 124c is distributed to the eight voxels 126 that are nearest neighbors to sample point 124c. Because FIG. 7a is representative of a two-dimensional slice of the volume, only four nearest-neighbor voxels, 126a to 126d, are shown in FIG. 7a.

The irradiance at sample point 124c is distributed to the eight nearest-neighbor voxels 126 by, for each nearest-neighbor voxel, calculating a distance from the sample point 124c to the voxel, using the distance to the voxel to calculate a contribution weight, and distributing an irradiance to that voxel that equals the irradiance at the sample point 124c multiplied by the contribution weight. The same contribution weight is used for each of the irradiance components, $I_r$, $I_g$, and $I_b$. In other embodiments, different contribution weights may be used for the different irradiance components.

If the sample point 124c is very near to the center of a particular one of the eight nearest-neighbor voxels 126, a high contribution weight is assigned to that voxel and a low contribution weight is assigned to each of the other nearest-neighbor voxels. If the sample point 124c is equidistant from all it eight nearest-neighbor voxels, an equal contribution weight of 0.125 is assigned to each of the eight nearest-neighbor voxels.

The calculation of contribution weight may be considered to be a way to partially assign the ray at a given sample point to each of a plurality of neighboring voxels. The contribution weight may represent the proportion of the ray (for example, 0.9 of a ray or 0.1 of a ray) that is assigned to a given voxel.

For each of the eight nearest-neighbor voxels 126, the lighting circuitry 26 stores a value for the contribution weight arising from sample point 124c, and a value for the irradiance distributed from sample point 124c.

The distribution of irradiance is repeated for each of sample points 124 on each of the rays 122. The determining of irradiance is an additive process. Multiple sample points and multiple rays will contribute irradiance energy to each voxel. For example, referring to FIG. 7a, voxel 126d may receive irradiance from sample points 124c, 124d, 124e and 124f. Voxel 126d may also receive irradiance from sample points 124 that lie on different rays 122 which are not shown in FIG. 7a. For each voxel, the lighting circuitry 26 stores a sum of the irradiance received from the different sample points (which in the present embodiment is stored as three irradiance components $I_r$, $I_g$, and $I_b$).

Voxel 126d receives a contribution weight from each of sample points 124c, 124d, 124e and 124f, and may also receive contribution weights from sample points 124 that lie on different rays 122. For each voxel, the lighting circuitry 26 stores a sum of the contribution weights received from the different sample points. In the present embodiment, the same contribution weight is used for each of the three irradiance components.

In the present embodiment, the method is performed discretely by calculating at points (in this embodiment, the points are voxels). In other embodiments, a distance to a line could be used to determine contribution weights instead of a distance to a point. Interpolating to points is only one way to implement the method and there are different possible implementations.

The sum of the contribution weights at a voxel may be considered to be representative of a ray density associated with the voxel. If a ray passes very near the center of a given voxel, a contribution weight of 0.9, representative of 0.9 of that portion of the ray, may be associated with that voxel. If a ray passes further away, a contribution weight of 0.1, representative of 0.1 of that portion of the ray, may be associated with that voxel. Therefore the sum of contribution weights may be seen as a sum of fractional numbers of rays in a given volume. The contribution weight received from one or more sample points on a given ray does not depend on the amount of virtual light energy that the ray has.

For simplicity, FIG. 6 and FIG. 7a have been illustrated using rays that do not scatter. However, in the present embodiment, scattering of rays is included in the lighting model. Scattering is simulated as well as direct illumination.

Figure 7B:
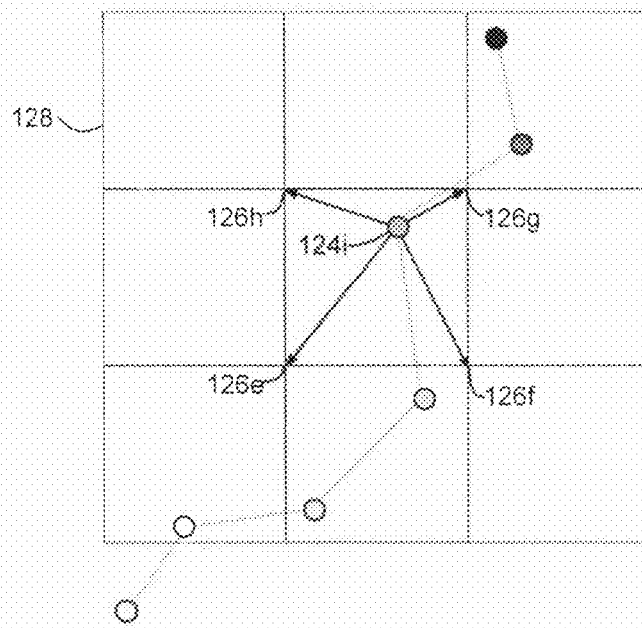
FIG. 7b is a schematic diagram of a ray passing through a volume, in which scattering is included.

At a given sample point, a ray may scatter rather than undergo absorption. A ray may scatter repeatedly as it traverses the volume. The extent of the scattering may be dependent on the material that the ray is scattering through (which may be determined based on intensity and/or incorporated in the absorption function). An example of a scattered ray is shown in FIG. 7b. Irradiance and contribution weights are calculated for each sample point, and irradiance is distributed to nearest-neighbor voxels in dependence on the contribution weights. For example, sample point 124i on the scattered ray distributes irradiance to voxels 126e, 126f, 126g and 126h by calculating contribution weights as described above.

In some embodiments, reflection may also be taken into account. In some embodiments, scattering and/or reflection may be omitted.

At stage 108, the lighting circuitry 26 calculates an adjusted irradiance at each voxel. As described above, each voxel has a total irradiance which is a sum of the irradiance contributions from each sample point near the voxel. Irradiance is accumulated over all sample points and all rays. Each voxel also has a total contribution weight which is a sum of the contribution weights from each sample point near the voxel, and may be considered to represent a ray density. The total contribution weight is accumulated in a separate channel to the red, blue and green irradiance channels. The total contribution weight may be considered to be a continuous value that represents the traversal aspect of the algorithm only. The total contribution weight may be considered to be a continuous value because the position of each sample point in space may take any value, and is not restricted to a grid. Therefore the contribution weight for each sample point may lie anywhere between 0 and 1 and is not, for example, rounded or quantized.

The lighting circuitry 26 calculates an adjusted irradiance for a given voxel by dividing the total irradiance at that voxel by the total contribution weight at that voxel, and then multiplying by a constant value. The constant value may be referred to as a scaling parameter, and is the same for all voxels. For each voxel, the lighting circuitry 26 divides the total irradiance for the voxel by the total contribution weight for that voxel, and then multiplies the result by the scaling parameter. In the present embodiment, the scaling parameter is 10. The scaling parameter may be chosen to obtain a desired lighting level.

The division of the total irradiance at each voxel by the total contribution weight at that voxel may be said to make the volume uniform. The volume may be uniform in the sense that an equal number of rays passes through each unit of volume. The dividing of the total irradiance by the total contribution weight and multiplying by a scaling parameter may be referred to as a normalization.

As discussed above, there are two effects that contribute to a decrease in intensity with distance from the virtual point light source 120. Firstly, each ray has a decreasing amount of virtual light energy as it gets further from the virtual point light source 120, because some of the virtual light energy is absorbed at each sample point. Secondly, the rays themselves become more widely separated as the distance from the virtual point light source increases (a fall-off according to the inverse square law). It may be considered that the density of the rays (the number of rays per unit volume) decreases as the distance from the virtual point light source increases. The adjustment of the irradiance at stage 108 is designed to compensate for the fall-off effect (the increasing ray separation) by normalizing the total contribution weight, which may be seen as adjusting the ray density at each voxel to a constant ray density (for example, 10 rays at each voxel).

However, the contribution weight for each ray is independent of the virtual light energy of each ray. For example, a ray that has a lot of virtual light energy and passes near a voxel may contribute a contribution weight of 0.9 from a sample point to that voxel and an irradiance value of 5 W/m$^3$. A ray that has less light energy and passes near to a voxel may still contribute a contribution weight of 0.9 from a sample point to that voxel, but may only contribute an irradiance value of 2 W/m$^3$. Therefore, differences in irradiance resulting from the decreasing energy of each ray are retained in the adjusted irradiance value, while differences in irradiance resulting from the different ray density are compensated for.

Adjusting irradiance in dependence on a ray density by using contribution weights may compensate for a fall-off in intensity due to the inverse square law. The total contribution weight can be used to normalize the energy (irradiance) channels.

FIGS. 8a, 8b, 8c and 8d are representative of counts and irradiance values for two voxels 130, 140 that are highlighted in FIG. 6. Voxel 130 is near to the virtual light source 120 and voxel 140 is further away from the virtual light source 120. It can be seen that there are fewer rays near voxel 140 than near voxel 130, and also that the rays near voxel 140 have less virtual light energy than the rays near voxel 130 (the decreased energy and redder color of the rays when further away from the virtual light source is represented by the darker color of the circles representing the sample points 124). The calculations on which FIGS. 8a, 8b, 8c, 8d are based are performed for a three-dimensional volume, even though FIG. 6 only shows a two-dimensional slice of that volume.

Figure 8A:
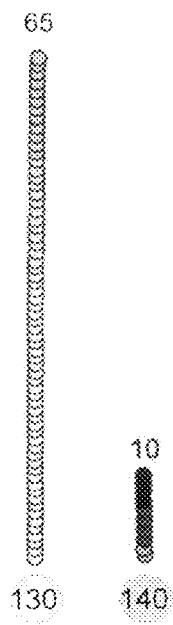
FIG. 8a represents a number of sample points contributing to each of two voxels on FIG. 6.

The two columns of FIG. 8a (for voxel 130 and voxel 140) each represent a number of sample points 124 that provide an irradiance contribution to the relevant voxel 130 or 140. Because of the spreading out of the rays, many more sample points contribute to voxel 130 than to voxel 140. In the example shown, 65 sample points contribute irradiance to voxel 130, and 10 sample points contribute irradiance to voxel 140. It can also be seen from the coloring of the sample points illustrated in FIG. 8a that the sample points contributing to voxel 130 have higher energy (shown by being paler in color) than the sample points contributing to voxel 140.

Figure 8B:
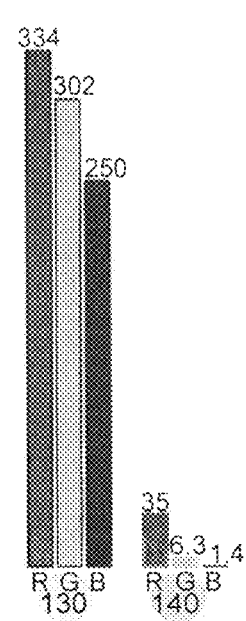
FIG. 8b represents spectral irradiance at each of two voxels on FIG. 6.

FIG. 8b is a histogram showing the spectral irradiance in W/m$^3$ at voxel 130 and at voxel 140. For each voxel, the spectral irradiance is divided into red, green and blue components $I_r$, $I_g$, and $I_b$, which are denoted by R, G and B in FIG. 8b. It may be seen that there is a large difference in irradiance between voxel 130 and voxel 140. For example, the red component $I_r$ is 334 W/m$^3$ at voxel 130 and 35 W/m$^3$ at voxel 140. The difference in irradiance results from the different number of sample points at voxel 130 and voxel 140, and also from the different amount of irradiance per sample point at voxel 130 and voxel 140.

Figure 8C:
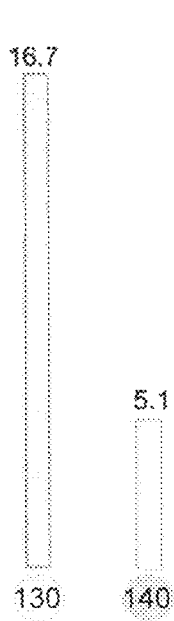
FIG. 8c represents a sum of contribution weights at each of two voxels on FIG. 6.

FIG. 8c is a histogram showing the total contribution weight at voxel 130 and at voxel 140. The total contribution weight is the sum of the contribution weights from all the samples represented in FIG. 8a. The total contribution weight at voxel 130 is 16.7. The total contribution weight for voxel 140 is 5.1. It may be seen that the difference in total contribution weights is smaller than the difference in irradiance. In this example, the total contribution weight for voxel 130 is about 3.3 times the total contribution weight for voxel 140, whereas the red component of irradiance, $I_r$, for voxel 130 is about 9.5 times the $I_r$ of voxel 140.

Figure 8D:
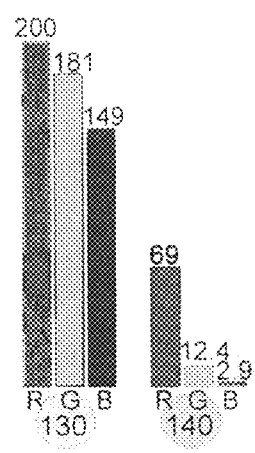
FIG. 8d represents normalized spectral irradiance at each of two voxels on FIG. 6.

FIG. 8*d* is a histogram showing an adjusted spectral irradiance (again broken down into R, G and B). For each voxel, the adjusted spectral irradiance has been obtained by dividing the spectral irradiance for that voxel by the total contribution weight for that voxel, and then multiplying by a scaling parameter. In this example, the value for the scaling parameter is 10. In other examples, any constant value may be used.

It may be seen that although the adjusted irradiance at point 130 is still larger than the adjusted irradiance at point 140, the difference between the adjusted irradiances is not as great as the difference between the original irradiances of FIG. 8*a*. For example, the original $I_r$ for voxel 130 is about 9.5 times the original $I_r$ for voxel 140, but the adjusted $I_r$ for voxel 130 is about 2.9 times the adjusted $I_r$ for voxel 140.

An adjusted irradiance value is individually obtained for each voxel in dependence on the total contribution weight at that voxel. The lighting circuitry 26 uses the adjusted irradiances for the voxels to construct an irradiance volume. The irradiance volume is independent of the viewpoint and depends only on the light source position and the voxel properties. Therefore the computation of the irradiance volume is capable of being used for multiple renderings from different viewpoints. The irradiance volume may be stored in data store 20.

At stage 110, the rendering circuitry 28 positions a virtual camera within the cavity. In other embodiments, the virtual camera may be placed at an earlier stage in the process of FIG. 5, or before the process of FIG. 5 is begun. The virtual camera is representative of a viewing position and orientation. In the present embodiment, the rendering circuitry 28 positions the virtual camera in accordance with an input from a user (for example, a clinician or radiologist). The user may specify the position and orientation of the virtual camera using any suitable input device. In alternative embodiments, the rendering circuitry may position the virtual camera automatically.

At stage 112, the rendering circuitry 28 renders an image based on the irradiance volume. The image is rendered as if viewed from the virtual camera. In the present embodiment, the image is a perspective projection image of the cavity. The rendering circuitry 28 casts rays from the camera into the volume represented by the volumetric imaging data set. Each ray may correspond to a pixel of a two-dimensional image data set that is to be obtained by the rendering of stage 114. Each ray from the camera steps through the volume represented by the volumetric imaging data set in increments of the voxel spacing. In other embodiments, a different spacing may be used.

For a given ray that is cast from the camera, the rendering circuitry 28 determines an irradiance at each of a series of incremental points along the ray. If the incremental point is representative of empty space the ray skips on to the next incremental point. The rendering circuitry determines the irradiance at each incremental point by interpolating the adjusted irradiance from neighboring voxels of the irradiance volume.

In the present embodiment eight nearest-neighbor voxels are considered in the interpolation for each incremental point. In other embodiments, a different number of voxels may be considered.

The rendering circuitry 28 integrates the irradiances determined for the incremental points along a ray from the camera to obtain a pixel color value for that ray. The determination of irradiance at each incremental point and the integration of irradiances is performed for each ray. The rendering circuitry 28 thereby determines a color value for each pixel in the two-dimensional image data set.

At stage 114, the display control circuitry 32 displays an image corresponding to the two-dimensional image data set on main display screen 16. The displayed image is an image of the cavity as illuminated by the point light source 74.

Applying the process of FIG. 5 when lighting an image of a cavity may result in a more uniform image, for example an image with reduced dynamic range. The dynamic range of a resulting rendered image may be controlled.

The normalization process may correct low level interference patterns that are caused by the traversal of rays through the volume. The normalization process may account for multiple light sources, volumetric light sources, and/or stochastic light sources. The normalization process may account for scattering.

By applying the process of FIG. 5, the fall-off of irradiance with distance to the point source may be modified. Points that are more remote from the virtual light source may become closer in irradiance to nearer points than would have been the case without the modification. Points which are remote from the virtual light source may be better lit than would have been the case without the modification. Better lighting may be lighting that makes an image that is provided to a user easier for the user to read. Better lighting may be lighting that causes the image that is provided to a user to show more regions of a structure of interest, or to show more detail in illuminated regions. By viewing an image that shows more regions or more detail and/or is easier to read, the user may find it easier to identify features of interest or to perform a diagnosis.

Using the process of FIG. 5 in imaging a cavity may allow more of the cavity to be seen than if no adjustment of irradiance is performed. By using perspective rendering, fish-eye rendering, or similar angular projections, it may be possible to visualize the wall of an extended structure such as a vessel. Using the process of FIG. 5 may allow more of that extended structure to be illuminated than would otherwise be the case. In an example in which the virtual point light is used to illuminate a vessel in a perspective projection, it may be possible for a user to see further down the vessel than would have been the case without the modification.

By adjusting irradiance individually at reference points in the volume rather than changing an exposure of the final rendered image, the effects of fall-off may be compensated for, while the effects of absorption may be unaffected. It may not be necessary to perform post-processing on the rendered image to change the dynamic range.

In some embodiments, an initial image of a region of interest, for example a cavity, is rendered without using an adjusted irradiance. The initial image is displayed to a user. The user may request calculation of an adjusted irradiance using any suitable input device, for example a trackball, rotary switch, mouse or keyboard. In some embodiments, the initial image is rendered using an adjusted irradiance and the user may use any suitable input device to change parameters as lighting parameters or adjustment parameters.

In some embodiments, the user may adjust lighting parameters such as the position of the light or the brightness of the lights. The user may request a change in overall light level. The lighting circuitry 26 may change the overall light level by changing the scaling parameter used in the calculation of the adjusted irradiance.

The user may change a value for an irradiance adjustment parameter. An irradiance adjustment parameter may be a parameter that affects the modification of the fall-off in irradiance with distance from a virtual light source. For example, an irradiance adjustment parameter may be a parameter in a function that is used to determine the adjusted irradiance from the original irradiance and the contribution weight. In some embodiments, the user may set different irradiance adjustment parameters for different color channels. In some embodiment, the user may set different irradiance adjustment parameters for different virtual light sources.

The user may change a color balance of an image. The lighting circuitry 26 may change the color balance by, for example, changing the relative absorption of red, green and blue components or scaling one of the adjusted red, green and blue irradiance components differently from another of the adjusted components.

In some embodiments, images are rendered in real time, i.e. while a scan is being performed. In such embodiments, any lighting parameters or irradiance adjustment requested by the user may be used for the current image and for subsequent images, unless the user makes a new request.

In the embodiment described above, the total irradiance at each voxel is adjusted at stage 108 by dividing by the contribution weight at the voxel and multiplying by a scaling parameter. This method of adjustment may be described as a complete normalization. The irradiance is adjusted as if there were a constant number of rays passing near each voxel. Fall-off effects that are the result of different numbers of rays may be removed.

In further embodiments, the normalization may be made partial so that some fall-off effects remain. In some embodiments, the adjusted irradiance is calculated by combining a non-normalized part and a normalized part. In one example, the non-normalized part of the adjusted irradiance is 50% of the irradiance value from stage 106. The normalized part of the adjusted irradiance is obtained by dividing the remaining 50% of the irradiance value by the total contribution weight and multiplying by a scaling parameter. The adjusted irradiance is calculated by adding together the normalized part and the non-normalized part. In some embodiments, the user may determine the relative size of the normalized part and the non-normalized part, for example by operating a slider.

In other embodiments, the irradiance may be adjusted by using any suitable function of the original irradiance and the contribution weight. For example, in one embodiment, the adjusted irradiance is calculated by dividing the original irradiance by a square root of the contribution weight, and then multiplying by a scaling parameter. In some embodiments, a user may select a function to be used. For example, the user may select a function from a plurality of pre-set functions. In some embodiments, a different function may be selected for one color channel than for another color channel. As a result, the modification of the fall-off may be different for one color than for another color.

By providing only a partial normalization, a desired lighting effect may be achieved. For example, in some circumstances, a virtual point light source having an inverse square law fall-off may result in too much dynamic range, but a virtual point light source in which the fall-off has been entirely removed may not have enough dynamic range. Therefore it may be desirable to achieve an intermediate effect.

The embodiments above describe a normalization process for illumination by a single virtual point light source. In other embodiments, more than one virtual point light source is placed within the volume, for example within a cavity. Multiple point light sources are placed at stage 104. At stages 104 and 106, rays are tracked from each of the point light sources and irradiances from sample points on the rays are distributed to neighboring voxel. In one embodiment, the lighting circuitry 26 records separately the irradiance and contribution weight resulting from each of the point light sources. For example, where there are two light sources, the lighting circuitry 26 records values for total irradiance components $I_{r1}$, $I_{g1}$, and $I_{b1}$ and total contribution weight resulting from the first light source, and values for total irradiance components $I_{r2}$, $I_{g2}$, and $I_{b2}$ resulting from the second light source. At stage 108, the lighting circuitry 26 calculates for each voxel a first adjusted irradiance associated with the first light source and a second adjusted irradiance associated with the second light source, and then sums the first adjusted irradiance and second adjusted irradiance to obtain a final irradiance for the voxel.

In an alternative embodiment, the lighting circuitry 26 records for each voxel a single total $I_r$, $I_g$, and $I_b$ and a single total contribution weight that do not discriminate by which contributions come from which light source. The adjusted irradiance is calculated by dividing the total irradiance (which may come partly from the first light source and partly from the second light source) by the total contribution weight (which may come partly from the first light source and partly from the second light source) and multiplying by a scaling parameter.

In some embodiments, different normalization may be applied to light from different point light sources. For example, a complete normalization may be applied to irradiance from one light source, and a partial normalization may be applied to irradiance from another light source. In some embodiments, lighting parameters related to each light source are individually adjustable by the user. In some embodiments, the user may operate a single control to change all of the light sources, for example to adjust the position of all the light sources or to reduce the brightness of all of the light sources. The controls offered to the sonographer may be made simpler by limiting the parameters that may be adjusted.

Although embodiments above are described with reference to point light sources, the method of FIG. 5 may also be applied to other types of virtual light sources, for example to volumetric light sources and/or to ambient lighting. Ambient lighting may comprise light coming from the exterior of the volume but from random directions (in some cases, slightly biased towards one direction).

The method of FIG. 5 is used to adjust irradiance in dependence on a ray density. By adjusting irradiance in dependence on a ray density, it is possible to compensate for the sharp fall-off in intensity with distance from a virtual point light source that is caused by the inverse square law. Although one method of calculating contribution weights is described above, any method that adjusts irradiance in dependence on a ray density may be used.

In alternative embodiments, after calculating irradiance at each voxel, a compensation factor may be calculated based on measured distance from the virtual point light source to the voxel. The compensation factor may be considered to be an approximate ray density. The irradiance can then be adjusted based on the compensation factor, for example by multiplying the irradiance by the square of the distance. Such a compensation factor based on distance may in principle be used to compensate for the inverse square law fall-off. However, it may be more difficult to take into account scattering using such an approach. In contrast, in the embodiment described in relation to FIG. 5, some regions may have an increased number of rays due to the presence of scattered rays, and thus scattering may be taken into account inherently. Furthermore, the use of a compensation factor based on an analytical distance relationship, rather than based on tracking individual rays such as described in relation to FIG. 5, may produce interference or quantization effects due to the placement of voxels on a grid.

Although embodiments described above comprise rendering of a cavity, the method of FIG. 5 may be used in the rendering of any volume which may or may not include an interior structure of the body. The method of FIG. 5 allows point light sources to be used with less fall-off that would otherwise be the case, which may improve the lighting characteristics of an image. The method of FIG. 5 may be combined with other lighting techniques. The method of FIG. 5 may be used in images of regions in which an occlusion is present. The method of FIG. 5 may be used in any suitable rendering process that involves perspective rendering, or rendering using a fish-eye or other related angular projection.

In some embodiments above, a virtual directional light source is placed outside a region of interest and the method of FIG. 3 is applied to the virtual directional light source. In some embodiments above, a virtual point light source is placed inside a region of interest and the method of FIG. 5 is applied to the virtual point light source. In some embodiments, the method of FIG. 3 and the method of FIG. 5 may both be applied to the same volumetric imaging data set simultaneously.

In one example, a virtual directional light source is placed outside a cavity and a virtual point light source is placed inside the cavity. The method of FIG. 3 is applied to the directional light source and is not applied to the point light source. The method of FIG. 5 is applied to the point light source and not to the directional light source. Irradiances from the directional light source (obtained using the method of FIG. 3) are combined with irradiances from the point light source (obtained using the method of FIG. 5) to form an irradiance volume. An image is rendered based on the irradiance volume.

In another example, a virtual point light source is placed outside a cavity and both the method of FIG. 3 and the method of FIG. 5 are applied to the virtual point light source. For rays emitted by the virtual point light source, no irradiance is calculated for a first portion of the rays outside the cavity. When the rays enter the cavity, irradiance is calculated. The calculated irradiance is then adjusted in dependence on ray density.

An irradiance volume is formed using the adjusted irradiances and an image is rendered based on the irradiance volume.

Any combination of the methods of FIG. 3 and FIG. 5 may be performed on any combination of virtual light sources. A single irradiance volume may have irradiance contributions from a plurality of virtual light sources. The irradiance contribution from each virtual light source may have been determined using the method of FIG. 3, the method of FIG. 5, or neither of the method of FIG. 3 or the method of FIG. 5.

The description above describes rendering of a single image based on an irradiance volume (and also based on other inputs which include the volumetric imaging data set). However, in a flythrough view, a series of images is displayed in which the viewpoint appears to move through the region of interest, for example moving through a cavity or along the length of a vessel.

A series of images may be rendered for a flythrough view using the process of FIG. 3, the process of FIG. 5, or a combination of the processes of FIG. 3 and FIG. 5.

In one embodiment in which a flythrough view is used, the data receiving circuitry 24 receives a volumetric imaging data set which is representative of an ultrasound scan of a three-dimensional region of a patient which comprises a vessel. The segmentation circuitry 30 obtains a segmentation of the vessel. The lighting circuitry 26 positions a plurality of virtual directional light sources outside the volume. The rendering circuitry 28 positions a virtual camera at a first position inside the vessel. The lighting circuitry 26 positions a virtual point light source inside the vessel, such that the point light source is co-located with the position of the virtual camera.

The positions of the various light sources may be related to each other, to the camera, and/or to the vessel. For example, a pair of directional light sources may be placed at a given angle relative to each other. One or more directional light sources may be placed at a given angle relative to a viewing direction of the virtual camera. The placing of the light sources may be determined in response to user input or automatically.

The lighting circuitry 26 obtains a first irradiance volume by casting rays from the virtual point light source and virtual directional light sources and determining irradiances as described above with reference to FIG. 3 (in other embodiments, the process of FIG. 5 may be used). In the present embodiment, the lighting circuitry 26 obtains the first irradiance volume (and subsequent irradiance volumes) using a global illumination lighting method.

The rendering circuitry 28 renders a first image based on the first irradiance volume, from the first position of the virtual camera. The rendering circuitry 28 then moves the position of the virtual camera to a second position within the vessel. The position of the virtual camera may be moved in response to a user input or automatically.

The lighting circuitry 26 updates the first irradiance volume to account for the change in position of the virtual point light source (which moves with the camera). The contribution of the directional light sources to the irradiance calculation is unchanged and does not need to be recalculated. The irradiance resulting from the point light source is calculated at its new position, and is combined with the irradiance from the directional light sources. The updated first irradiance volume may be referred to as a second irradiance volume. The rendering circuitry 28 renders a second image based on the second irradiance volume.

Once again, the rendering circuitry 28 moves the position of the virtual camera (and hence the position of the point light source), the lighting circuitry 26 calculates an updated (third) irradiance volume to take account of the movement of the point light source, and the rendering circuitry 28 renders a new image from the new virtual camera position using the newly updated (third) irradiance volume. This movement of the virtual camera and associated processing is repeated to create a flythrough view in which the camera position moves down the vessel.

In the present embodiment, the rendering circuitry 28 changes the position of the virtual camera in response to user input. In other embodiments, the rendering circuitry 28 may change the position of the virtual camera automatically, for example by moving the virtual camera along a vessel centerline.

In the present embodiment, only one segmentation of the vessel is obtained. In other embodiments, segmentations may be obtained repeatedly as the camera moves through the interior structure of interest. For example, flood fill segmentations may be obtained starting from each of a succession of virtual camera positions.

In the present embodiment, only the point light source moves as the virtual camera is moved and a series of images is rendered. The positioning of the plurality of directional light sources stays the same for all the images. In an alternative embodiment, the positioning of the directional light sources is tied to the position of the virtual camera. Therefore, when the virtual camera moves, the directional light sources also move. For example, when the viewing direction of the virtual camera relative to the volume is changed, the angle of the directional light sources also changes.

In some embodiments, all the virtual light sources (directional light sources or point light sources) remain static while a camera position moves. In such embodiments, it may not be necessary to recalculate the irradiance volume when the camera position moves. The rendering circuitry 28 may render a new image based on the existing irradiance volume. In other embodiments, some or all virtual light sources move when the camera moves. The movement of the virtual light sources may or may not be tied to the movement of the camera.

In some embodiments, a user places a start point for a flythrough view, and the rendering circuitry 28 renders a flythrough view automatically (which may be described as an autopilot function). The flythrough view comprises navigation through an interior structure such as a cavity, duct, lumen, airway or vessel. A user may take over control by moving a trackball to change a direction of flight. In some embodiments, a user may manually navigate through the interior structure using the console's rotary switches.

In some embodiments, the lighting circuitry 26 generates a first irradiance volume and the rendering circuitry 28 renders a static image based on the first irradiance volume. The user may adjust lighting parameters (for example, the position or brightness of each virtual light source) using any appropriate user input device before a flythrough view is started. In other embodiments, the user changes lighting parameters during a flythrough view. In further embodiments, the user may change any appropriate parameters before or during a flythrough view. For example, the user may change a lighting angle, a lighting position, an irradiance adjustment parameter, a scaling parameter or a color balance parameter.

Combining global illumination with a flythrough view may provide usable lighting settings which may effectively illuminate a pathology and its surroundings. The method of FIG. 3 may be used to provide fill lighting within an interior structure. The method of FIG. 5 may be used to provide improved illumination through reduced fall-off of irradiance with distance. A combination of point lighting and fill lighting may provide a natural lighting effect with a desired light level, which may effectively illuminate areas of interest.

In some embodiments, a rendered image of an unfolded view may be provided in addition to or instead of an endoscopic or flythrough view. An unfolded view may be a two-dimensional map in which a surface of a three-dimensional interior structure (for example, the wall of the colon) is displayed as a two-dimensional structure.

In some embodiments, the lighting circuitry 26 performs simulated lighting of the interior structure as described above, in three-dimensional space. The lighting circuitry 26 calculates irradiance for each of a plurality of points on a surface of the interior structure. The surface of the interior structure is then unfolded such that all the points on the surface are represented by corresponding points on a plane. The rendering circuitry 28 uses the irradiances that were calculated in three dimensions in rendering an image of the point on the plane. In one embodiment, the structure of interest is the colon, and a strip of light is placed along the colon. The strip of light may be treated as multiple light sources. In some embodiments, both a flythrough view and an unfolded view are displayed to the user. In such embodiments, using the same lighting for the flythrough view and the unfolded view may make it easier for the user to relate features of the flythrough view to features of the unfolded view.

In other embodiments, the surface of the interior structure is unfolded before a lighting simulation is carried out. The lighting circuitry 26 then lights the unfolded surface using one or more virtual light sources. The light source or sources may appear to be placed above the two-dimensional unfolded surface. In further embodiments, the lighting of an unfolded surface may comprise a first lighting process which is performed before the surface is unfolded and a second lighting process which is performed after the surface is unfolded.

Embodiments above are described in relation to a cavity. However, the region of interest may be any suitable structure of the body for which illumination is required. For example, the region of interest may be an interior structure of the body such as a cavity, a duct, a lumen, an airway or a vessel.

The method incorporating features of the method of FIG. 3 and/or features of the method of FIG. 5 may be used for a number of different medical applications. For example, in some embodiments, the interior structure of interest is the gall bladder and the method may be used to view gallstones. In some embodiments, the interior structure is a vessel and the method may be used to view obstructions or holes in the vessel. The method may be used to view regions of narrowing, for example regions of stenosis. In some embodiments, the interior structure is the colon and the method may be used to view abnormal structures in the wall of the colon, for example polyps. In some embodiment, the region of interest is the uterus and the method may be used to look for uterus malformations or to see whether IVF (in vitro fertilization) has been successful. In some embodiments, the method may be used for airway imaging, for example for assessing lunch disease or lung nodules. In some embodiments, the method may be used to image sinuses. Any suitable imaging modality may be used.

In embodiments described above, the generation of an irradiance volume and rendering of an image based on the irradiance volume comprises a global illumination method. In other embodiments, the generation of the irradiance volume and/or the image rendering may comprise at least one of global illumination, photon mapping, light space volume traversal, deep shadow maps, half angle slicing, light propagation volumes or shadow propagation volumes.

Although the above embodiments are described in the context of rendering ultrasound images, the method of FIG. 3 and/or FIG. 5 may be used to render images from data of any appropriate modality, for example CT, MR, PET or SPECT. The volumetric imaging data set may be derived from any appropriate medical imaging scan of the human or animal body.

In other embodiments, the method of FIG. 3 and/or FIG. 5 may be used to render images from other volumetric imaging data sets that are not derived from a medical imaging scan. In some embodiments, the method of FIG. 3 and/or FIG. 5 may be used to render images from volumetric imaging data that is representative of at least part of the human or animal body but that is not derived from a medical imaging scan, for example virtual anatomy data. In some embodiments, the method of FIG. 3 and/or FIG. 5 may be used to render images from volumetric imaging data sets comprising any suitable type of data.

Certain embodiments comprise a medical imaging apparatus comprising an ultrasound volume capture capability and capable of providing a flythrough view and/or an unfolded view. A volume rendered image is generated using a global illumination method. In some embodiments, the generation of the volume rendered image comprises the use of one or more directional lights originating outside the volume, where the lighting simulation is suspended until the light reaches a cavity or region of interest. In some embodiments, the medical imaging apparatus performs a method incorporating a photon mapping method which generates an irradiance volume, and by tracking a reference contribution weight the irradiance is normalized to a fixed potential energy.

Whilst particular circuitry has been described herein, in alternative embodiments functionality of one or more of circuitries can be provided by a single processing resource or other component, or functionality provided by a single circuitry can be provided by two or more processing resources or other components in combination. Reference to a single circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. An image processing apparatus comprising
data receiving circuitry configured to receive a volumetric imaging data set which is representative of a volume, the volume comprising a region of interest; and
lighting circuitry configured to place a virtual light source outside the region of interest, and to apply a lighting simulation process to simulate light from the virtual light source;
wherein the applying of the lighting simulation process is at least partially different for a first lighting region than for a second lighting region, the first lighting region comprising at least part of the volume outside the region of interest and the second lighting region comprising at least part of the region of interest, and
wherein the lighting simulation process comprises casting a plurality of rays from the virtual light source and wherein, for each of the plurality of rays, applying the lighting simulation process is at least partially different for a first portion of the ray than for a second portion of the ray, wherein at least part of the first portion of the ray is within the first lighting region and at least part of the second portion of the ray is within the second lighting region, and wherein applying the lighting simulation process for each ray comprises determining irradiance at each of a plurality of sample points along the second portion of the ray and at least one of a) and b):
a) calculating no irradiance for the first portion of the ray;
b) determining irradiance at each of a plurality of sample points along the first portion of the ray, wherein the irradiance is based on a reduced absorption.

2. An apparatus according to claim 1, wherein the applying of the lighting simulation process is at least partially different for the first lighting region than for the second lighting region to ensure that at least one of a), b), c) and d);
a) at least some of the light from the virtual light source reaches the region of interest;
b) the illumination of the region of interest is increased;
c) a desired light level is achieved inside the region of interest;
d) the virtual light source illuminates at least one selected part of the region of interest.

3. An apparatus according to claim 1, wherein the volumetric imaging data set is representative of a medical imaging scan of the volume.

4. An apparatus according to claim 3, wherein the medical imaging scan comprises at least one of an ultrasound scan, a CT scan, an MR scan, a PET scan, a SPECT scan.

5. An apparatus according to claim 1, wherein the region of interest comprises at least one of an interior anatomical structure, a body cavity, a duct, a vessel, a lumen, an airway, an air-filled region, a fluid-filled region.

6. An apparatus according to claim 1, wherein applying the lighting simulation process in the first lighting region comprises at least one of a) or b):—
a) reducing absorption of the light within the first lighting region;
b) providing substantially no absorption of the light within the first lighting region.

7. An apparatus according to claim 1 wherein the first lighting region comprises a region between the virtual light source and the region of interest.

8. An apparatus according to claim 1 wherein the first lighting region includes a part of the region of interest.

9. An apparatus according to claim 1 wherein a boundary of the second lighting region is within the region of interest and is displaced from a boundary of the region of interest by an offset distance.

10. An apparatus according to claim 1, wherein the applying of the lighting simulation process is varied gradually across a transition region between the first lighting region and the second lighting region, such that the lighting simulation process transitions gradually from the lighting simulation process for the first lighting region to the lighting simulation process for the second lighting region.

11. An apparatus according to claim 1, further comprising rendering circuitry configured to render at least one image based on the simulated light.

12. An apparatus according to claim 11, wherein the lighting circuitry is further configured to use the simulated light to generate an irradiance volume corresponding to the volumetric imaging data set, wherein the rendering circuitry is configured to render the at least one image at least partly based on the irradiance volume, and wherein at least one of the generation of the irradiance volume and the rendering of the image comprises at least one of: global illumination, photon mapping, light space volume traversal, deep shadow maps, half angle slicing, light propagation volumes, shadow propagation volumes.

13. An apparatus according to claim 11, wherein the virtual light source comprises a virtual directional light source, the lighting circuitry is further configured to place a virtual point light source within the region of interest, and the rendering circuitry is configured to render an image based on both simulated light from the virtual point light source and simulated light from the virtual directional light source.

14. An apparatus according to claim 11, wherein the at least one image comprises a series of images used to generate a flythrough view, and wherein a position of the virtual light source remains static with respect to the volume in each of the series of images.

15. An apparatus according to claim 11, wherein the at least one image comprises a series of images used to generate a flythrough view, and wherein a position of the virtual light source with respect to the volume is different in at least some of the series of images.

16. An apparatus according to claim 11, wherein the at least one image comprises an unfolded view.

17. An apparatus according to claim 11, wherein the at least one image comprises at least one of a perspective projection, a fish-eye projection, an angular projection.

18. An apparatus according to claim 1, wherein at least one of a) and b):
   a) the lighting circuitry is configured to place the virtual light source at least one of 1) a selected angle or a predetermined angle, 2) a selected position or a predetermined position; and 3) a light direction relative to at least one of the region of interest and a virtual camera position;
   b) the lighting circuitry is configured to place the virtual light source in response to user input.

19. An apparatus according to claim 1, wherein the lighting circuitry is further configured to place at least one further virtual light source relative to the volume and, for the or each further virtual light source, to apply the lighting simulation process to simulate light from the further light source, wherein the applying of the lighting simulation process is at least partially different for a further at least part of the volume outside the region of interest than for a further at least part of the region of interest.

20. An apparatus according to claim 1, wherein the volumetric imaging data set comprises data acquired using a contrast medium.

21. An image processing apparatus comprising
   data receiving circuitry configured to receive a volumetric imaging data set which is representative of a volume, the volume comprising a region of interest; and
   lighting circuitry configured to place a virtual light source outside the region of interest, and to apply a lighting simulation process to simulate light from the virtual light source;
   wherein the applying of the lighting simulation process is at least partially different for a first lighting region than for a second lighting region, the first lighting region comprising at least part of the volume outside the region of interest and the second lighting region comprising at least part of the region of interest, and
   wherein the lighting circuitry is further configured to place at least one further virtual light source relative to the volume and, for the or each further virtual light source, to apply the lighting simulation process to simulate light from the further light source, wherein the applying of the lighting simulation process is at least partially different for a further at least part of the volume outside the region of interest than for a further at least part of the region of interest,
   wherein at least one of a), b) and c):
   a) the lighting circuitry is configured to place the virtual light source and the at least one further virtual light source at least one of 1) a selected angle or a predetermined angle and 2) a position or a lighting direction relative to each other;
   b) the lighting circuitry is configured to place the virtual light source and the at least one further virtual light source at least one of 1) a selected angle or a predetermined angle and 2) a position or a lighting direction relative to at least one of the region of interest and a virtual camera position;
   c) the lighting circuitry is configured to place the virtual light source and the at least one virtual light source in response to user input.

22. An image processing apparatus, comprising
   data receiving circuitry configured to receive a volumetric imaging data set which is representative of a volume; and
   lighting circuitry configured to place at least one virtual light source relative to the volume and to apply a lighting simulation process to simulate light from the virtual light source,
   the lighting simulation process comprising simulating a plurality of rays emitted from the virtual light source, calculating irradiance resulting from the rays at each of an array of reference points in the volume, and adjusting the calculated irradiance for at least some of the array of reference points, thereby to modify a fall-off in irradiance with distance from the virtual light source, wherein
   the lighting simulation process further comprises partially attributing each ray to each of a plurality of neighboring reference points,
   each ray is partially assigned to each of the plurality of neighboring reference points based on a contribution weight for the ray at each of the neighboring reference points, and
   the adjusting of the calculated irradiance at a reference point is in dependence on a ray density associated with the reference point, and wherein the ray density at each reference point comprises or is representative of a sum of contribution weights from different ones of the plurality of rays.

23. An apparatus according to claim 22, wherein the modification of the fall-off in irradiance is to ensure that at least one of a) and b):
   a) the calculated irradiance values for reference points that are further from the virtual light source is closer to the calculated irradiance values of reference points that are closer to the virtual light source than would have been the case without the adjustment;
   b) reference points that are remote from the virtual light source are better lit than would have been the case without the adjustment.

24. An apparatus according to claim 22, wherein the adjusting of the calculated irradiance at a reference point is in dependence on a ray density associated with the reference point.

25. An apparatus according to claim 24, wherein, for each of the array of reference points, the ray density associated with the reference point comprises or is representative of a number of rays passing through a volumetric region associated with the reference point.

26. An apparatus according to claim 24, wherein the ray density includes a contribution from scattered rays.

27. An apparatus according to claim 22, wherein, for each ray, the adjustment of the calculated irradiance resulting from the ray is independent of the virtual light energy of the ray.

28. An apparatus according to claim 22, wherein adjusting the calculated irradiance for a reference point comprises dividing at least part of the calculated irradiance for the reference point by the sum of contribution weights for the reference point and multiplying by a scaling parameter.

29. An apparatus according to claim 22, wherein the volumetric imaging data set is representative of a medical imaging scan of the volume.

30. An apparatus according to claim 22, wherein the volumetric imaging data set is representative of a region of interest comprising at least one of a cavity, a duct, a vessel, a lumen, an airway, an air-filled region, a fluid-filled region.

31. An apparatus according to claim 30, wherein the lighting circuitry is configured to place the at least one virtual light source inside the region of interest.

32. An apparatus according to claim 22, wherein the lighting circuitry is further configured to use the adjusted irradiance values to construct an irradiance volume, and wherein the apparatus further comprises rendering circuitry configured to render at least one image, wherein the rendering is at least partly based on the irradiance volume.

33. An apparatus according to claim 32, wherein the at least one image comprises a series of images which are used to generate a flythrough view, each constructed from a respective irradiance volume, and wherein a position of the at least one virtual light source with respect to the volume is different in at least some of the series of images.

34. An apparatus according to claim 32, wherein the at least one image comprises an unfolded view.

35. An apparatus according to claim 32, wherein the at least one image comprises at least one of a perspective projection, a fish-eye projection, an angular projection.

36. An apparatus according to claim 22, wherein placing at least one virtual light source comprises placing a plurality of virtual light sources, wherein calculating irradiance comprises calculating a respective irradiance associated with each of the plurality of virtual light sources, and wherein adjusting the calculated irradiance comprises adjusting a respective irradiance associated with each virtual light source in dependence on a respective ray density associated with that virtual light source.

37. An apparatus according to claim 22, wherein the lighting circuitry is configured to select or adjust in response to user input at least one of a lighting angle, a lighting position, an irradiance adjustment parameter, the modification of the fall-off in irradiance with distance, a scaling parameter, a color balance parameter.

38. An apparatus according to claim 22, wherein the irradiance comprises a plurality of color channels, and irradiance is calculated and adjusted separately for each of the plurality of color channels.

39. An apparatus according to claim 38, wherein the adjustment of irradiance is different for different color channels, thereby to modify a fall-off in irradiance differently for different color channels.

40. An apparatus according to Claim 29, wherein the medical imaging scan comprises at least one of an ultrasound scan, a CT scan, an MR scan, a PET scan, a SPECT scan.

41. An image processing apparatus, comprising
data receiving circuitry configured to receive a volumetric imaging data set which is representative of a volume; and
lighting circuitry configured to place at least one virtual light source relative to the volume and to apply a lighting simulation process to simulate light from the virtual light source,
the lighting simulation process comprising simulating a plurality of rays emitted from the virtual light source, calculating irradiance resulting from the rays at each of an array of reference points in the volume, and adjusting the calculated irradiance for at least some of the array of reference points, thereby to modify a fall-off in irradiance with distance from the virtual light source,
wherein the adjusting of the calculated irradiance at a reference point is in dependence on a ray density associated with the reference point,
wherein adjusting the calculated irradiance at a reference point in dependence on a ray density comprises increasing irradiance for reference points having lower ray densities in relation to irradiances for reference points having higher ray densities.

42. An image processing apparatus, comprising
data receiving circuitry configured receive a volumetric imaging data set which is representative of a volume; and
lighting circuitry configured to place at least one virtual light source relative to the volume and to apply a lighting simulation process to simulate light from the virtual light source,
the lighting simulation process comprising simulating a plurality of rays emitted from the virtual light source, calculating irradiance resulting from the rays at each of an array of reference points in the volume, and adjusting the calculated irradiance for at least some of the array of reference points, thereby to modify a fall-off in irradiance with distance from the virtual light source, wherein
the lighting simulation process further comprises partially attributing each ray to each of a plurality of neighboring reference points,
each ray is partially assigned to each of the plurality of neighboring reference points based on a contribution weight for the ray at each of the neighboring reference points, and
the adjusting the calculated irradiance for a reference point comprises dividing at least part of the calculated irradiance for the reference point by the sum of contribution weights for the reference point and multiplying by a scaling parameter.

* * * * *